(12) United States Patent
Green et al.

(10) Patent No.: US 6,584,414 B1
(45) Date of Patent: Jun. 24, 2003

(54) PARKING LOT PAVEMENT ANALYSIS SYSTEM

(76) Inventors: Harold C. Green, 14111 Green Rd., Glyndon, MD (US) 21071; Charles W. Schwartz, 1112 E. Capital St., NE., Washington, DC (US) 20002; Douglas A. Gardner, 2313 Sandel La., Westminster, MD (US) 21157; Daniel J. Shaw, 13622 Gilbride La., Clarksville, MD (US) 21029

( * ) Notice: Subject to any disclaimer, the term of this patent is extended or adjusted under 35 U.S.C. 154(b) by 0 days.

(21) Appl. No.: 09/384,626

(22) Filed: Aug. 27, 1999

Related U.S. Application Data

(60) Provisional application No. 60/098,244, filed on Aug. 28, 1998.

(51) Int. Cl.[7] ................................................. G01B 5/00
(52) U.S. Cl. .......................................... 702/33; 701/207
(58) Field of Search .............................. 702/33, 34, 40, 702/42; 701/207; 342/22; 73/146; 703/2, 5, 6; 707/104.1; 340/941

(56) References Cited

U.S. PATENT DOCUMENTS

| | | | | |
|---|---|---|---|---|
| 4,899,296 A | * | 2/1990 | Khattak | ...................... 702/40 |
| 5,287,740 A | * | 2/1994 | Tomita | ......................... 73/146 |
| 5,614,670 A | * | 3/1997 | Nazaian et al. | ............... 73/146 |
| 5,753,808 A | * | 5/1998 | Johnson | ........................ 73/146 |

* cited by examiner

Primary Examiner—Marc S. Hoff
Assistant Examiner—Mohamed Charioui
(74) Attorney, Agent, or Firm—Law Offices of Royal W. Craig

(57) ABSTRACT

An improved parking lot pavement analysis system is described that analyzes field survey data and generates a report which provides the necessary information to make the most cost-effective maintenance and repair decisions for commercial and residential parking lots. The pavement analysis system can be implemented on an existing PC computer to provide a user-friendly way of standardizing and guiding the visual survey and pavement sampling to determine existing conditions. The pavement analysis system guides entry of data indicating the pavement's existing condition, and then calculates and recommends maintenance and repair options. The calculations are based on an expert diagnostic system analysis which substantially reduces the requirement for expert interpretation. A complete life cycle cost analysis is performed, and this allows the user to make an informed decision about what type repairs are most appropriate for a particular situation. A comprehensive standardized, easy to read, report can be printed to convey sufficient information to enable a parking lot manager to time repairs with pinpoint accuracy.

21 Claims, 21 Drawing Sheets

PLPMS

Select Project

| Property Name | Street | City | State | ZIP | Project No. |
|---|---|---|---|---|---|
| Majestic Industrial Center | 5400 Eisenhower Ave. | Alexandria | VA | 20200 | 1235 |
| Test Project | 123 Wherever Ave. | Anytown | MD | 20000 | 96M.077 |
| The White House | 1600 Pennsylvania Ave. | Washington | DC | 20202 | 123456 |
| U. Md. Engineering Building | Campus Drive | College Park | MC | 20742 | 123-45 |
| Wal-Mart | 9999 Shop-Til-You-Drop Lane | Palookaville | OH | 30303 | WM-001 |

New

Edit

Delete

Cancel

FIG. 4

PLPMS

File   Edit   Reports   Window   Help

Majestic Industrial Center (Project No. 96M 077)

| Project Info 5 | Sections 10 | PCI Survey 15A | Core Data 15B | FWD Data 15C | Repair Options 25 | Repair Costs 30 | Report 35 |

Property

Name: Majestic Industrial Center

Description:

Street: 5400 Eisenhower Avenue

City: Alexandria    State: VA    Zip: 20200

Type: Industrial    Construction Date:

Property Manager

Company: University of Maryland

Street: Department of Civil Engineering

City: College Park    State: MD    Zip: 20742

Contact: Dr. G. Baecher    Ph: 3014051978

Title: Chairman    Fax: 3014052585

Project ID

Project No.: 96M.077

Preparer: Doug Gardner

Date: 10/16/19

Notes

This is based upon the FEA prototype reports.

FIG. 5

PLPMS

File  Edit  Reports  Window  Help

Majestic Industrial Center (Project No. 96M.077)

| Project Info 5 | Sections 10 | PCI Survey 15A | Core Data 15B | FWD Data 15C | Repair Options 25 | Repair Costs 30 | Report 35 |

| Label | Description | Area (sf) | Annual ESALs |
|---|---|---|---|
| ▲ Dock | Truck loading dock | 45000 | 10000 |
| Lot | Main parking area | 90000 | 200 |
| Lanes | Parking lot travel lanes | 12000 | 12000 |
| * | | | |

Edit Repair Unit Costs

Repair Type: Full Overlay ▶

Expected Life: 20      Cost Unit: sy-in

Cost item        Unit Cost

AC               $3.00

Close

FIG. 20

Edit Repair Criteria

Local Repair Criteria

Option 1 (Without Overlay)

| Distress | Sev | Min Dens | Max PCI | Repair |
|---|---|---|---|---|
| Alligator Cracking | H | 1 | 100 | Full Depth Repair |
| Alligator Cracking | L | 0 | 100 | Partial Depth Repa |
| Alligator Cracking | M | 0 | 100 | Full Depth Repair |
| Depression | H | 5 | 100 | Full Depth Repair |
| Depression | L | 0 | 100 | Do Nothing |
| Depression | M | 0 | 100 | Partial Depth Repa |
| L&T Cracking | H | 0 | 100 | Clean & Fill Cracks |

Option 1 (With Overlay)

| Distress | Sev | Min Dens | Max PCI | Repair |
|---|---|---|---|---|
| Alligator Cracking | H | 0 | 100 | Full Depth Repair |
| Alligator Cracking | L | 0 | 100 | Fabric |
| Alligator Cracking | M | 0 | 100 | Partial Depth Repa |
| Depression | H | 0 | 100 | Full Depth Repair |
| Depression | L | 0 | 100 | Do Nothing |
| Depression | M | 0 | 100 | Partial Depth Repa |
| L&T Cracking | H | 0 | 100 | Clean & Fill Cracks |

Option 2 (Without Overlay)

| Distress | Sev | Min Dens | Max PCI | Repair |
|---|---|---|---|---|
| Alligator Cracking | H | 0 | 100 | Partial Depth R |
| Alligator Cracking | L | 0 | 100 | Clean & Fill Cra |
| Alligator Cracking | M | 0 | 100 | Partial Depth R |
| Depression | H | 0 | 100 | Partial Depth R |
| Depression | L | 0 | 100 | Do Nothing |
| Depression | M | 0 | 100 | Shallow Depth |
| L&T Cracking | H | 0 | 100 | Do Nothing |

Option 2 (With Overlay)

| Distress | Sev | Min Dens | Max PCI | Repair |
|---|---|---|---|---|
| Alligator Crackin | H | 0 | 100 | Partial Depth Repa |
| Alligator Crackin | L | 0 | 100 | Do Nothing |
| Alligator Crackin | M | 0 | 100 | Shallow Depth w/ |
| Depression | H | 0 | 100 | Partial Depth Repa |
| Depression | L | 0 | 100 | Do Nothing |
| Depression | M | 0 | 100 | Shallow Depth Rej |
| L&T Cracking | H | 0 | 100 | Clean & Fill Cracks |

PCI Trigger Values

Overlay: 55   Reconstruction: 20   Reclamation: 20

Close

FIG. 21

PARKING LOT PAVEMENT ANALYSIS SYSTEM

CROSS-REFERENCE TO RELATED APPLICATIONS

The present application derives priority from U.S. Provisional Patent Application No. 60/098,244 for "PARKING LOT PAVEMENT ANALYSIS SYSTEM"; filed: Aug. 28, 1998.

BACKGROUND OF THE INVENTION

1. Field of the Invention

The present invention relates to computer-based evaluation and reporting systems and, more particularly, to a computerized parking lot pavement analysis and reporting system for minimizing the effort and cost of parking lot maintenance and repair.

2. Description of the Background

The importance of pavement management in commercial and residential markets is becoming more evident as managers are realizing that preventative maintenance can help to maximize one's original investment in private roads, parking lots and the like. The underlying concept is that preventative measures executed at specific points can reduce the need for subsequent more expensive repairs at later periods. This is clear from the chart shown in FIG. 1 which illustrates the life cycle of a typical asphalt pavement.

The pavement condition is generally rated by PCI (a conventional pavement condition index along a scale of 0–100). Generally, repair of structural distresses followed by an overlay should occur when the PCI pavement rating drops to between 50 and 70. Otherwise, the rate of failure for repair cost increases significantly as the pavement continues to age. Thus, proper timing of the repairs will result in lower maintenance cost over the life of the pavement.

Traditional methods of pavement management in commercial and residential markets being with inspection of the condition of pavement to determine the size and shapes of surface distress features such as longitudinal cracks, transverse cracks, alligator cracks, seam cracks, potholes and the like. Typically, an engineer performs an inspection and prepares a written analysis for their client with repair options.

There have been prior efforts at standardizing the evaluation process. For example U.S. Pat. No. 5,447,336 to Deighton shows a road pavement management tool including a set of forms to be filled out which simplify analysis of pavement conditions and recommended treatments.

More extensive efforts include U.S. Pat. No. 4,899,296 to Khattak which discloses a pavement inspection apparatus for inspecting the condition of pavement using a vehicle and two video array cameras that project downward onto the pavement. The apparatus includes distress feature analysis electronics for determining the size, shape and location of surface distress features and to evaluate such features against preset standard values to determine the severity of distress.

There is also a wealth of authority discussing the various objective approaches and models for pavement analysis. See, for instance, Witczak et al., *Evaluation of the SHRP Pavement Performance Models,* Proceedings 8$^{th}$ International Conference of the Structural Analysis of Pavements, Seattle, Wash., August, 1997; Rada et al, Airport *Pavement Management: Meeting Agency Woods,* ASCE Transportation '95 Congress, San Diego, Calif., October, 1995; Schwartz et al., *Joining Dynamically Segmented Infrastructure Data in Relational Database Systems,* Second ASCE Congress on Computing in Civil Engineering, Atlanta, Ga., June, 1995, pp. 468–477; Smith et al., *Development of the Delaware DOT Pavement Management System,* Transportation Research Record, No. 1397, 1993, pp. 54–62; Schwartz, C. W., *Infrastructure Condition Forecasting Using Neural Networks,* ASCE Infrastructure Management-New Challenges, New Methods, Denver, June, 1993, pp. 282–284; Rada et al., *Integrated Pavement Management System for Kennedy International Airport,* Journal of Transportation Engineering, ASCE, Vol. 118, No. 5. September/October, 1992, pp. 666–685; Schwartz et al.,*"Database Organization for Airfield Pavement Management,* Seventh Conference on Computing in Civil Engineering, ASCE, Washington, D.C., May, 1991, pp. 16–24; Rada et al., *Analysis of Climate Effects on the Performance of Unpaved Roads,* Journal of Transportation Engineering, ASCE, Vol. 115, No. 4, July, 1989, pp, 389–410.

The foregoing authority goes so far as to suggest certain database management techniques and computer implemented models for analysis of roadways and airport runways. However, the models are loosely implemented with commercial database programs. The programs are very complex and are geared for analysis of public highways. Implementation and use requires the participation of skilled programmers.

There is one known software pavement design program called DARWin 3.0. DARWin performs a wide range of calculations including a complete life cycle cost analysis for each design alternative. The DARWin program is divided into the following four modules, each of which addresses a specific item in the overall pavement design process.

A flexible structural design module can be used to design and analyze asphalt concrete pavements.

A rigid structural design module is used to design and analyze Portland cement concrete pavements. The program directly calculates the required slab thickness based on the given design inputs.

An overlay design module allows the design of seven different overlay types.

A life cycle cost module is an analytical tool that can be used to compare alternative designs. All costs are considered in the analysis, including initial construction costs, maintenance costs, rehabilitation costs, and salvage values. The results can be output using different evaluation methods. Cash flow diagrams can be generated automatically for each project.

Unfortunately, the DARWin software is application specific and is geared for building roadway with the longest life per dollar spent. On the other hand, existing commercial roads and parking lots account for more paved area than roads. As yet, there are no known computerized analysis and reporting systems geared specifically for maintenance and repair of existing pavement, nor are there any systems designed specifically for commercial parking lot management. The only traditional way to get a completely unbiased assessment of a parking lot is to hire an engineer to evaluate the pavement and to get his hand-written report on his findings.

It would be greatly advantageous to provide a computerized user-friendly system to standardize and guide visual surveying and pavement sampling to determine existing conditions, to take the resulting data, analyze the same, and generate a comprehensive report outlining appropriate repair scenarios for the end customer.

SUMMARY OF THE INVENTION

It is, therefore, an object of the present invention to provide a parking lot pavement analysis system that can be implemented on an existing PC computer to provide a user-friendly way of standardizing and guiding the visual survey and pavement sampling to determine existing conditions, to take the resulting data and analyze the same, and to generate a report outlining appropriate repair scenarios for the end customer.

It is another object to enable faster data collection, input, analysis, manipulation for consideration of different repair scenarios, and engineered solutions with comprehensive cost analysis for each alternative.

It is another object to subject the collected data to an expert diagnostic system analysis to substantially reduce the requirement for expert assistance, and to eliminate guesswork from the process, and to yield consistent and repeatable results.

It is a further object to provide a standardized, easy to read, comprehensive report containing sufficient information to enable a customer to time repairs with pinpoint accuracy.

It is another object to provide a tool capable of providing value-engineered pavement solutions, including the capability to design a pavement that will last for a specified period of time.

In accordance with the above objects, an improved parking lot pavement analysis system is provided. The pavement analysis system organizes the collection of field survey data, analyzes the same, and generates a report which provides the necessary information to make the most cost-effective maintenance and repair decisions for commercial and residential parking lots. The information includes the following:

Existing Conditions

Life Cycle Cost Analysis (including current cost, future cost, and life cycle cost)

Pricing Alternatives (including engineered, value engineered and do nothing options).

Maintenance and Rehabilitation Design Options.

To accomplish the above most effectively, the pavement analysis system allows consideration of three different repair options: Engineered Repair; Value Repair; and Do Nothing. "Engineered Repair" is based upon repair strategies and pavement design thickness using published industry recommendations.

"Value Repair" represents alternative repair procedures which have been used by the private industry. The long term reliability of some of these repair methods has not been extensively studied. This option therefore offers a greater degree of risk.

The third option is to "Do Nothing". This represents the condition of the pavement in the event that no repairs are performed. The present system compares the different repair scenarios for life cycle cost implications and recommends the most cost-effective type of repair for each section. This allows the user to make an informed decision about what type repairs are most appropriate for each particular situation.

BRIEF DESCRIPTION OF THE DRAWINGS

Other objects, features, and advantages of the present invention will become more apparent from the following detailed description of the preferred embodiment and certain modifications thereof when taken together with the accompanying drawings in which:

FIG. 4 is the Select Project Screen for opening or creating projects.

FIG. 5 is the Index tab Interface 2 which displays an indexed portfolio of computerized forms by which each of the software modules of FIG. 2 can be accessed, navigated and used for analysis.

FIG. 6 is the Sections information form for spread sheet entry of project sections.

FIG. 7 is the PCI Survey data entry and analysis form which must be completed for a base Level 1 analysis.

FIG. 18 shows the Repair Costs data window which displays a compilation of repair costs on a section-by-section basis.

FIG. 20 is the Edit Repair Unit Costs screen for setting up initial unit cost parameters.

FIG. 21 is the Edit Repair Criteria screen for setting up decision tree criteria used by the Repair Options/Decision tree module 200 in making repair recommendations.

DETAILED DESCRIPTION OF THE PREFERRED EMBODIMENTS

Figure 1:
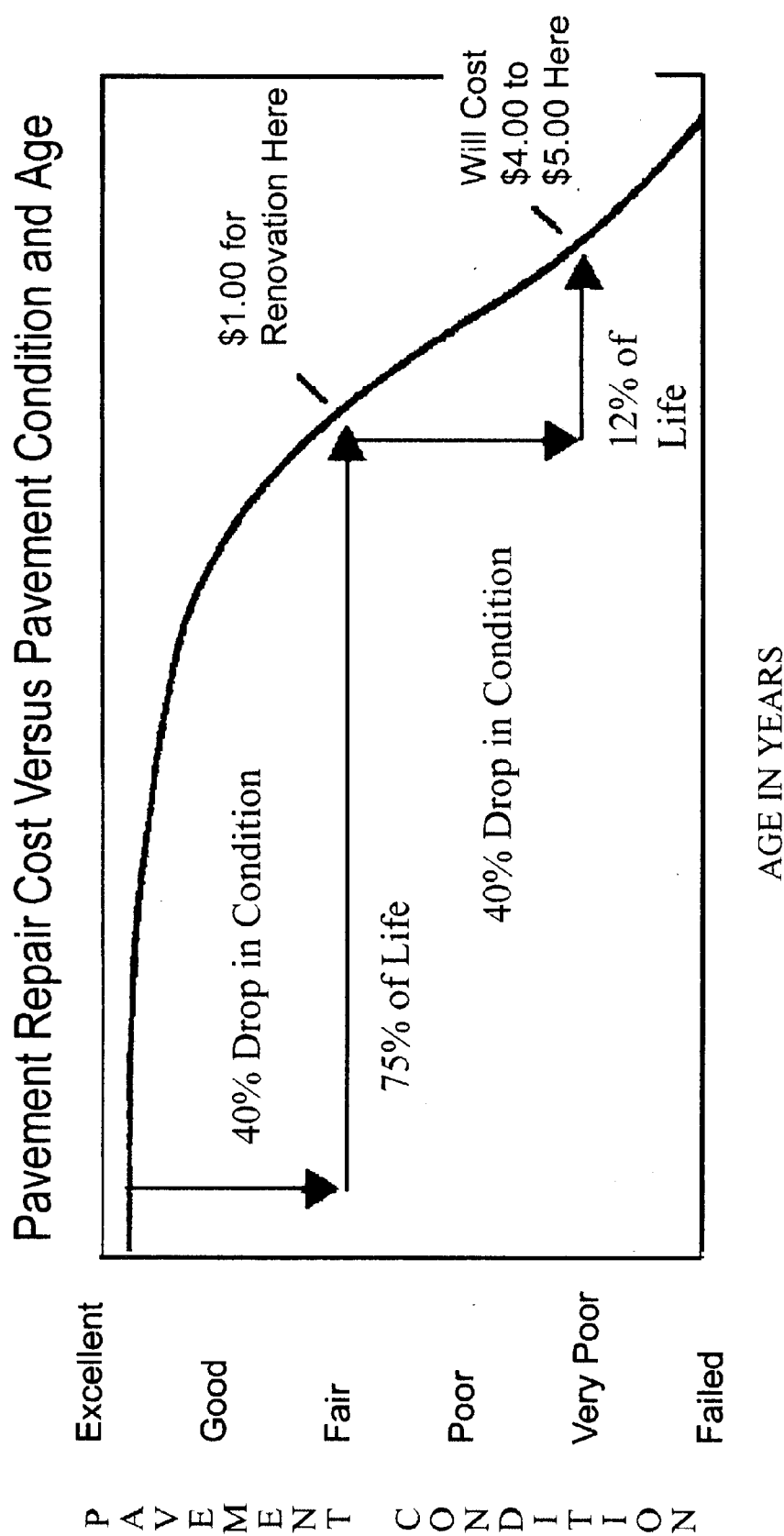
FIG. 1 is a chart illustrating the life cycle of a typical asphalt pavement.

The present invention is a computerized Pavement Profile System for standardizing and guiding visual surveying and pavement sampling to determine existing conditions, to take the resulting data, analyze the same, and generate a report outlining appropriate repair scenarios. The Pavement Profile System is designed as a business tool to speed the collection and sorting of data (including the Pavement Condition Index), and to analyze the extent and severity of pavement to be repaired, and to provide varied options to repair or rehabilitate the pavement structure.

The benefits of the Pavement Profile System over conventional manual processes currently utilized within the industry are as follows:

faster data collection and input;

California Bearing Ratio (CBR) values are used.

default data (assumptive-based) and curves may be used in lieu of actual data;

repairs can be timed with pinpoint accuracy;

analysis can be based on three levels of field survey detail, and considers three hypothetical repair options;

lot can be segmented into different regions with different repair outcomes for greater flexibility;

a standardized, easy to read, comprehensive report;

an expert diagnostic software program for instant analysis and reserve studies;

The Pavement Profile System is intended for use by the engineers who perform the field surveys in order to help generate a comprehensive report for their customers. The system guides the engineers in taking the field surveys, standardizes data collection and reporting procedures, and it analyzes the data in a unique manner to compare the value of repair options. The information is presented in a comprehensive report for the engineer's customers that can be easily understood by lay persons.

The Pavement Profile System includes a conventional computer workstation, operating system, and the software-implemented process of the present invention (the PPS software). The computer workstation may be, for example, a conventional personal computer with standard internal components, e.g., an Intel Pentium microprocessor with peripheral chipset mounted on an appropriate motherboard. Of course, other more or less powerful computer systems can be used, but it is suggested that minimum system performance is realized with a 66 Mhz CPU processor with 8 Mb of RAM. Approximately 10 Mb of storage is required, and this may be in the form of conventional hard disk storage. The user interface is preferably a conventional color monitor, and a standard input device such as a mouse. The operating system is preferably Windows 95 or a like system.

The PPS software may be compressed onto a series of installation floppy diskettes or a CD-ROM, and may be loaded onto a computer system as described above using conventional installation macros such as provided with Windows 95.

As explained, initial pavement survey data collection in the field is required prior to substantive use of the PPS system. The PPS software is designed to facilitate three levels of data collection and analysis as desired by the user.

A Level 1 analysis is a basic level that summarizes pavement condition as determined from visual distress surveys and incorporates minimal design evaluation. The level 1 analysis requires a visual assessment of all of the asphalt pavement areas to determine the quantity and severity of distresses. Default values are provided based on assumptions.

A Level 2 analysis is an intermediate level that involves a higher level of pavement condition data gathering (e.g., visual distress surveys plus field cores) combined with a more thorough design evaluation. Level 2 requires an assessment of the Pavement Condition Index (PCI) as described above for each distinct portion of the pavement, plus additional coring of the pavement at representative locations for the purpose of determining the pavement thickness and to obtain samples of the underlying soil subgrade materials. Each soil sample must be visually classified and at least one representative sample tested to determine the California Bearing Ratio (CBR).

A Level 3 analysis is the highest level and requires both of the above-described visual distress surveys and core sampling, plus additional subgrade strength testing and non-destructive testing (using, for example, a Falling Weight Deflectometer).

The collected data is entered, analyzed, and the pavement design options are compared based on life cycle cost estimates. To accomplish its analysis, the system considers three different repair options: Engineered Repair; Value Repair; and Do Nothing.

"Engineered Repair" is based upon repair strategies and pavement design thickness using published industry recommendations.

"Value Repair" represents alternative repair procedures which have been used by the private industry. The long term reliability of some of these repair methods has not been extensively studied. While less expensive at the outset, the Value Repair option therefore offers a greater degree of risk in the long run.

The third option is to "Do Nothing". This represents the condition of the pavement in the event that no repairs are performed.

The system compares the different repair scenarios for life cycle cost implications and gives three options from which the user can select the most cost-effective type of repair for each section. This allows the user to make an informed decision about what type repairs are most appropriate for each particular situation. The software accomplishes data collection, analysis and reporting via a series of modules, each module being dedicated to a particular function.

Figure 2:
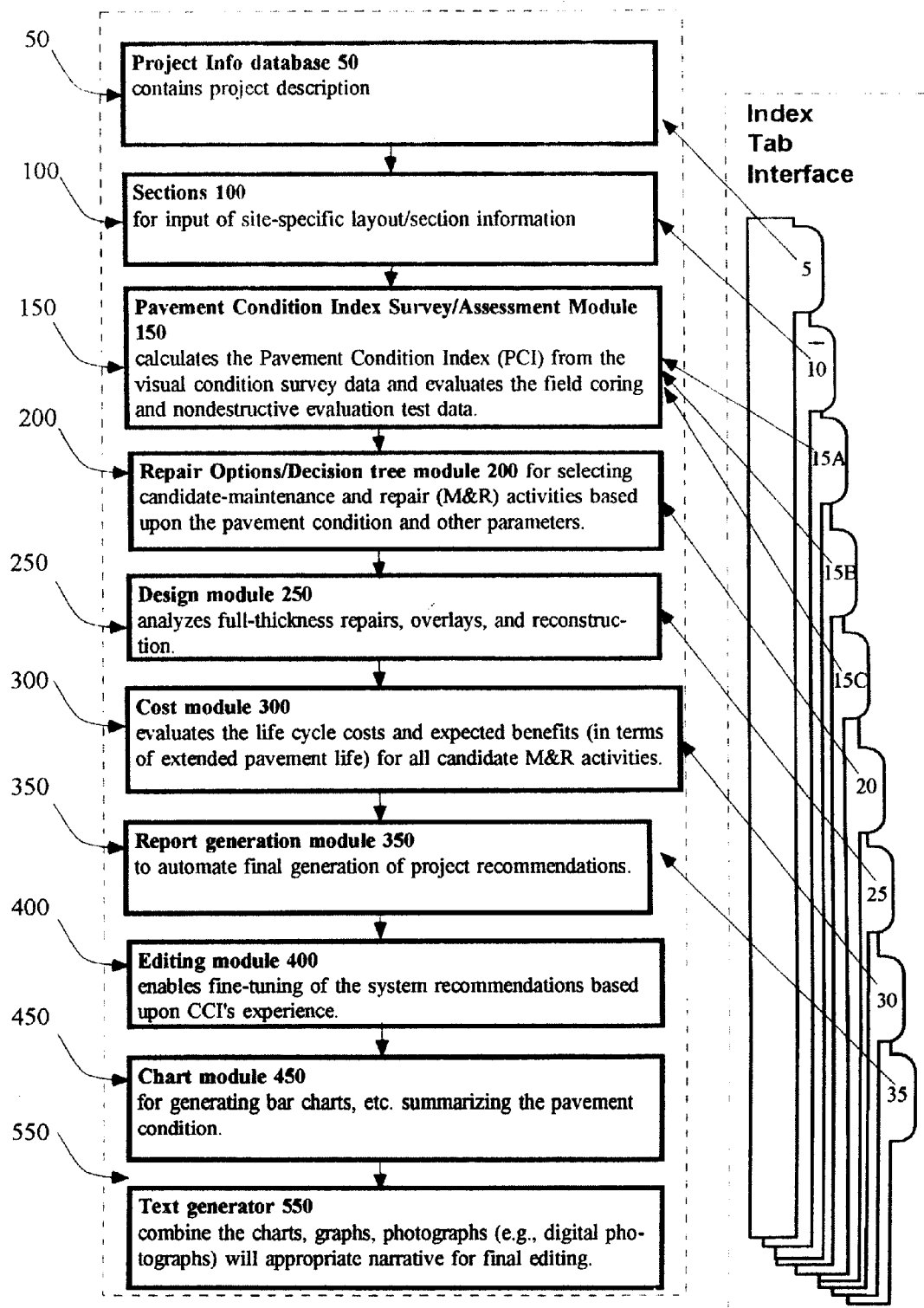
FIG. 2 is a block diagram that illustrates the interrelationship of the various modules of the pavement analysis system according to the present invention.

FIG. 2 is a block diagram that illustrates the interrelationship of the various modules. As shown in FIG. 2, the modules are as follows.

A Project Info database module 50 is a database containing a full description of each project.

A Sections module 100 coordinates entry of site-specific layout/section information.

A Pavement Condition Index Survey/Assessment Module 150 coordinates entry of visual survey and field test data in accordance with the desired Level 1–3 of analysis, calculates the Pavement Condition Index (PCI) from the visual condition survey data, and analyzes field coring and non-destructive evaluation test data.

A Repair Options/Decision tree module 200 further analyzes data from the Pavement Condition Index Survey/Assessment Module 150 and recommends a selection of candidate-maintenance and repair (M&R) activities based upon pavement condition and other parameters.

A Design module 250 analyzes full-thickness repairs, overlays, and reconstruction.

A Cost Module 300 evaluates the life cycle costs and expected benefits (in terms of extended pavement life) for all candidate maintenance and repair activities.

A Report generation module 350 automates final generation of project recommendations. The Report generation module 350 incorporates a number of sub-modules, including an editing module 400 that enables manual fine-tuning of report recommendations based upon the engineer's experience, a Chart module 450 for generating bar charts, etc., all of which graphically summarize the pavement condition, and a text generator 550 for combining the charts, graphs, photographs (e.g., digital photographs) with appropriate text narrative for final editing.

All of the above-described modules can be conveniently accessed via a graphical Index tab Interface 2. The Index tab Interface 2 comprises a series of selectable index tabs 5–35 which provide direct access to selected modules. While the user is free to navigate the modules in any desired order, the tabs 5–35 are arranged to sequentially guide the user through all of the necessary data entry and analysis modules to produce a useful and comprehensive report.

Figure 3:
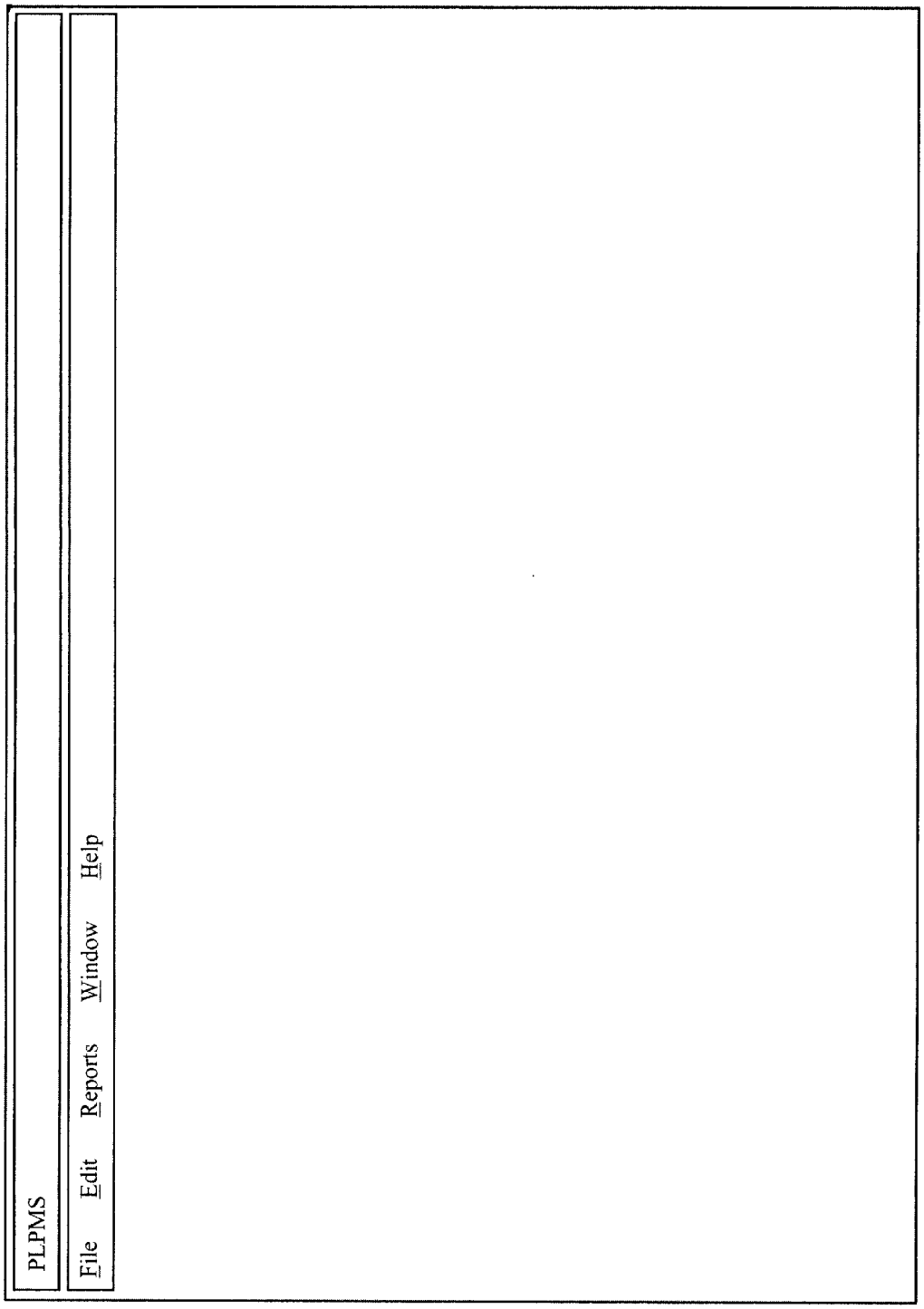
FIG. 3 is the initial PLPMS Setup Screen.

Once the field survey has been performed and the software installed and started, the program initializes to the blank PPS Setup Screen shown in FIG. 3. The PPS Setup Screen of FIG. 3 displays five command line options at the top, including File, Edit, Reports, Window, and Help.

By selecting the Edit command, the user can edit certain pre-defined system set-up parameters upon which the ultimate analysis and report are based, and this capability will be described more fully. The Reports command allows the user to generate a Full Project report or a pavement Condition report as will also be described. The Help command is a context-sensitive assistance feature that essentially provides immediate graphical assistance in interpreting the various other commands and menu items.

By selecting the File command, the user is confronted with a number of options by which he can Open an existing project or define a new one, Close a project (if already opened), Export a project database to a variety of other file formats, Import data from a variety of other file formats, Print the program Setup parameters, Print the current screen, or Exit the program.

To Open an existing project or define a new one, the user selects File > Open. The Select Project Screen of FIG. 4 arises, and a spread sheet listing of all predefined projects appears with accompanying descriptive information. The descriptive information appears in fields across the screen including a Property Name, Street, City, State (ST), Zip and Project No.

Four push-buttons appear to the right of the descriptive information, and these include New, Edit, Delete and Cancel. The user can create a new project by depressing New, and this action places the cursor in the Property Name field in a newly created and blank row. The user can manually enter all of the requisite fields and may tab from field to field. Alternatively, the user can open a pre-existing project by clicking on the appropriate row. This highlights the row, and the user may double-click the row or push the Edit button to open the selected project. A Delete button is also provided to delete selected projects, and a Cancel button is provided to cancel undesired actions.

Once the user has created a new project or opened a pre-existing project, for example, by double-clicking the "Majestic Industrial Center" project, the Index tab Interface 2 of FIG. 5 arises. The Index tab Interface 2 of FIG. 5 displays an indexed portfolio of computerized forms by which each of the software modules of FIG. 2 can be conveniently accessed, navigated and used for analysis.

The Index tab Interface 2 initializes to the Project Info tab 5, which reveals an open project information form for entering project information into the Project Info Database 50. The project information form is arranged in four primary sections including a Property section, a Property Manager section, a Project ID section, and project associated Notes. The Property section comprises a number of property-specific descriptive fields such as Name ("Majestic Industrial Center"), optional property Description, Street, City, State, ZIP, and Construction date. In addition, drop down list of selectable project "Types" is provided with choices such as "Industrial", "Residential", "Commercial", etc. The Property Manager section comprises a number of descriptive fields devoted to the managing authority including Company ("University of Maryland"), Street, City, State, Zip, Individual contact, Title, Phone and Facsimile numbers. The Project ID section contains a user-assigned Project No., Preparer, and Date. An optional Notes section is provided for entry of any desired notations.

Once all of the appropriate project information has been entered, the user may proceed to the Sections module 100 by depressing the adjacent Sections Tab 10. This reveals an open Sections information form as in FIG. 6 for spread sheet entry. The Sections information form of FIG.6 is in spread sheet format and allows tabular entry of the various pavement sections into the Sections module 100 (FIG. 2). Each section is defined in the Label column and the various pavement sections are identified as "Dock", "Lot", "Lanes" etc. A Description column follows the Label, and this allows entry of a textual description of each section. The section area is defined next (in square feet), and this is followed by the Daily Equivalent Single Axel Loads is ("ESALs" . . . a conventional measure of traffic loading). While the ESAL value may be defined by the user, the default values are as shown in the following table:

| DEFAULT ESAL VALUES FOR PPS PROGRAM | | | |
|---|---|---|---|
| PROPERTY TYPE | SOLID BODY trucks per day | TRACTOR TRAILER trucks per day | TOTAL ESALs per year |
| MULTIFAMILY | 20 | 5 | 7939 |
| OFFICE | 40 | 10 | 15,877 |
| RETAIL | 50 | 20 | 26,389 |
| COMMERCIAL | 40 | 30 | 33,324 |
| INDUSTRIAL | 20 | 70 | 64,641 |

Notes:
1. Front axle loads for solid body assumed to be 6,000 lbs.
2. Rear axle loads for solid body trucks assumed to be 15,000 lbs., single axle.
3. Truck factor for solid body = 0.49
4. Front axis loads for tractor trailers assumed to be 12,000 lbs.
5. Rear axle loads for each tandem rear axis for tractor trailer assumed to be 34,000 lbs.
6. Truck factor for tractor trailers = 2.39
7. Trash trucks are included with tractor trailers The above-described section information allows the Sections Module 100 to break the project down and analyze maintenance and repair options by specific sections, each of which may endure different amounts of traffic, and may be prone to (or already exhibit) different types and degrees of stress.

Figure 7:
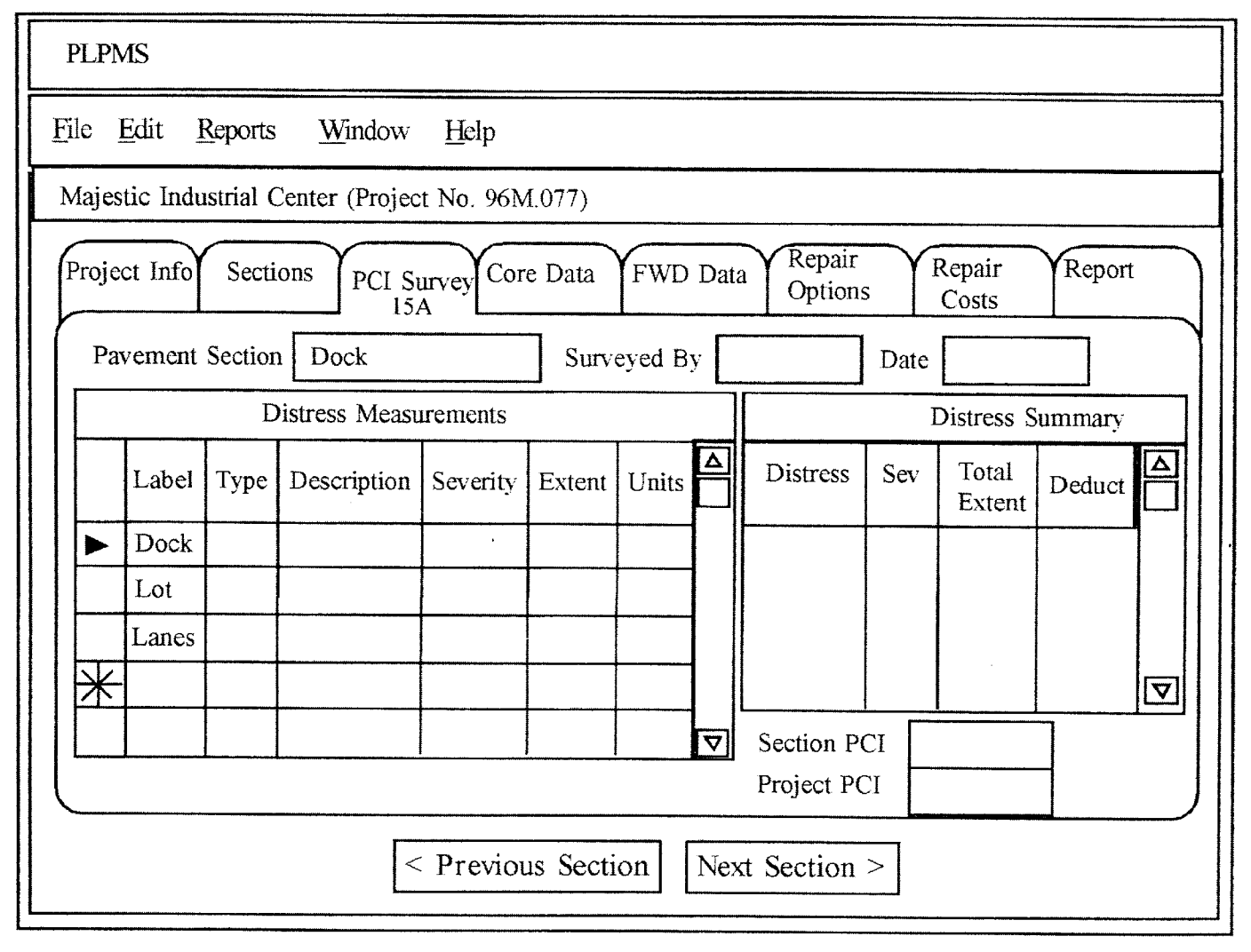

"Once all of the project section information has been entered, the user may proceed to the Pavement Condition Index Survey/Assessment Module 150. The Pavement Condition Index Survey/Assessment Module 150 is accessed by three different tabs appearing in the Index tab Interface 2. The first of the three is the PCI Survey tab 15A, and this opens the PCI Survey data entry and analysis form of FIG. 7 which is completed by the user for a base Level 1 analysis. To complete the PCI Survey form, the user will have conducted visual distress surveys of the project on a section-by section basis, thereby allowing assessment of all of the asphalt pavement areas to determine the quantity and severity of distresses. The survey should include a separate visual inspection of the condition of the sidewalks, curbing, and drainage structures. A separate PCI Survey form is completed for each section defined in the Sections information form of FIG. 6. A <Previous Section button and adjacent >Next Section button at the bottom allow the user to move between sections, and the current section is identified in a Pavement Section block at top left. A "Surveyed By" block is located to the immediate right to allow entry of the surveyor's identity, and this is followed by a "Date" block to date the section survey. All noted distresses are entered into the "Distress Measurements" section at left, and this further includes a spread sheet array of fields beginning with a user-selectable Label. Following entry of a Label, the user indicates the particular type of distress in two linked "Type" and "Description" fields. The Description block is a drop-down window of various pre-defined distress types. Existing common distress types include Alligator cracking, Bleeding, Block Cracking, Depression, L&T Cracking, Patching, Potholes, Rutting, Slip/Shove/Corrugation, and Weather/Raveling (Paver—U.S. Corps. Of Engineers). Each pre-defined distress type is associated with a number identifier, and this is displayed in the Type block immediately preceding. User selection of the Type block will automatically fill in the corresponding Description field, and vice versa. The next adjacent Severity block is a drop-down box that allows the user to indicate the severity of the distress from low "L", to medium "M" and high "H". Finally, the user may specify the Extent of the distress in units such as linear feet, square feet, etc. All distress information input for each section is summarized to the right in a Distress Summary area, and for each type of distress the Distress Summary area identifies the type of Distress, states the Severity, sums the Total Extent of the identified Distress per section, and calculates an appropriate deduction from a perfect Pavement Condition Index (PCI) of 100. Immediately below at lower right, the Section PCI is calculated based on the sum deductions for the displayed section, and the overall project PCI is calculated from deductions for all sections."

Figure 8:
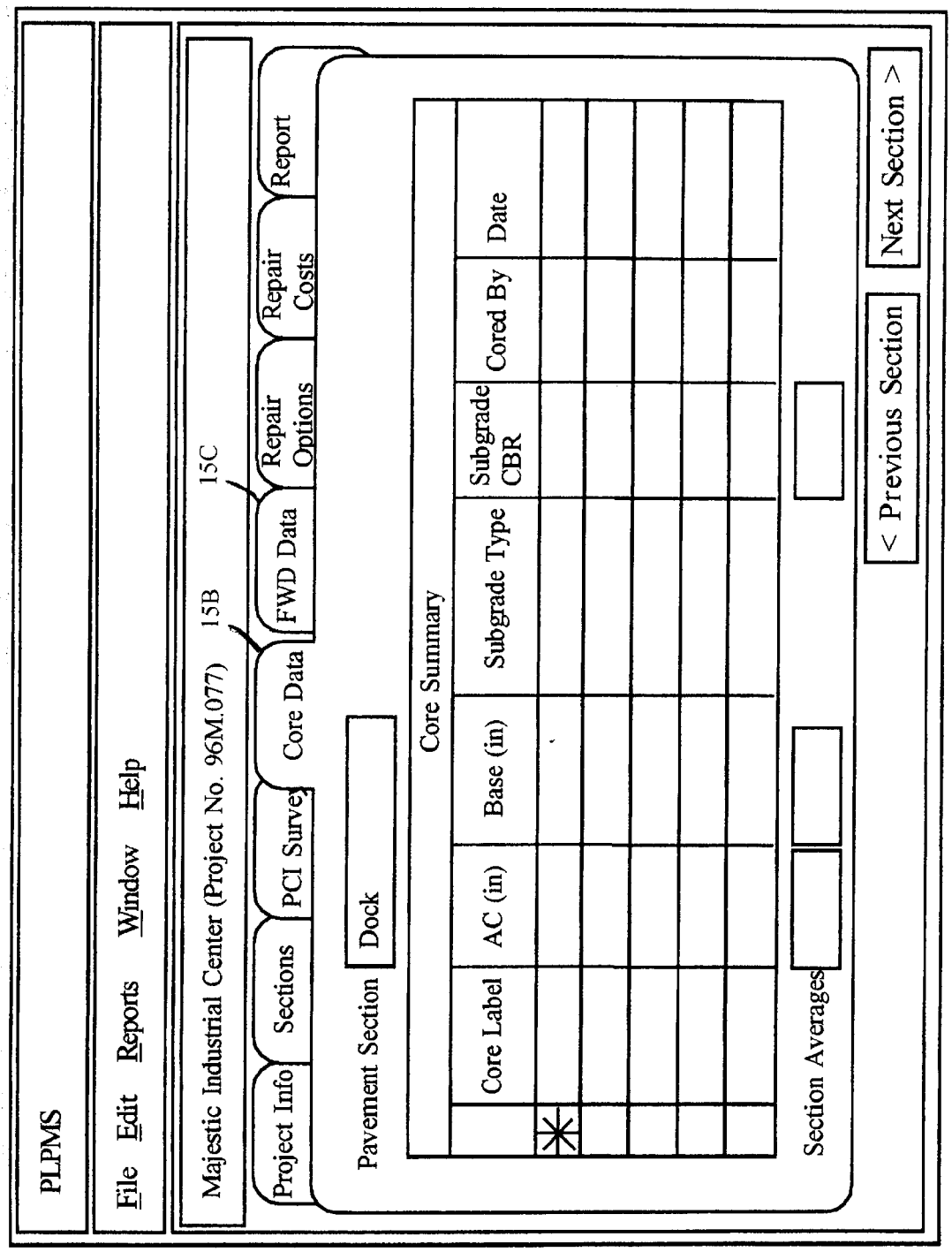
FIG. 8 is the Core Data entry and analysis form which must be completed for an intermediate Level 2 analysis.

If the user wishes to complete a heightened Level 2 analysis, he must additionally select the second of the three PCI Survey tabs which is the Core Data Survey tab 15B. This opens the Core Data entry and analysis form of FIG. 8 which must be completed for an intermediate Level 2 analysis. To complete the Core Data Survey form, the user must have conducted core sampling and subgrade strength testing on a section-by section basis, thereby allowing physical sampling of all of the asphalt pavement areas to determine the core data. The physical data necessary to complete the level 2 analysis includes the number of core samplings taken, analysis thereof to determine asphalt thickness, base thickness/type, soil type, general suitability of soil type, measured CBR value, swell percentage, maximum compacted soil density, moisture content, and swell value. Given such field data, a separate Core Data Survey form must be completed for each section defined in the Sections information form of FIG. 6. A <Previous Section button and adjacent >Next Section buttons at lower right allow the user to move between sections, and the current section is identified in a Pavement Section block at top left. All core data is entered into the Core Summary section in the center, and this further includes a spread sheet array of fields beginning with a user-selectable Core Label. Following entry of a Label, the user indicates for each core sample taken the particular asphalt thickness "AC" (in inches), and base thickness "Base" (in inches). The Subgrade type is entered to the right, and this box consists of a drop-down list of pre-defined subgrades[1] including "Good subgrade—generic", "Fair subgrade—generic", "Poor subgrade—generic", "Well-graded gravel (GW)", "Poorly-graded gravel (GP)", "Silty Gravel (GM)", "Clayey Gravel (GC)", "Well-graded sand (SW)", "Poorly Graded Sand (SP)", "Siltey Sand (SM)", "Clayey Sand (SC)", "Silt (ML)", "Clayey Silt (MH)", "Lean Clay (CL)", "Fat Clay (CH)", "Organic Silt/Lean Clay (OH)", and Fat Organic Clay (OL)". The subgrade California Bearing Ratio (CBR) as measured by the core sample is entered to the right, and this is followed by fields indicating Cored By (the core surveyor) and the date on which the core sample was taken. The section averages for the AC (in inches), Base measurement (in inches), and subgrade California Bearing Ratio (CBR) are shown below. While the CBR value may be defined by the user, there are default values pre-loaded in the database as shown in the following table:

| DEFAULT CBR VALUES FOR PPS PROGRAM | | | | |
|---|---|---|---|---|
| VISUAL CLASSIFICATION | GRAVEL | SAND | SILT | CLAY |
| AASHTO CLASSIFICATION | A-1, A-2 | A-1, A-2, A-3 | A-4, A-5 | A-6, A-7 |
| CBR RANGE | 20–80 | 10–40 | 4–20 | 0–15 |
| CBR USED FOR DESIGN | 20 | 10 | 6 | 3 |
| RATING AS SUBGRADE | EXCELLENT | GOOD | FAIR | POOR |

Notes:
1. Information is intended to provide a general guide and is not intended to cover all situations. Laboratory determination of the CBR is recommended.

[1]While various other subgrade classifications may be used, the present system uses ASHTO standard classifications.

Figure 9:
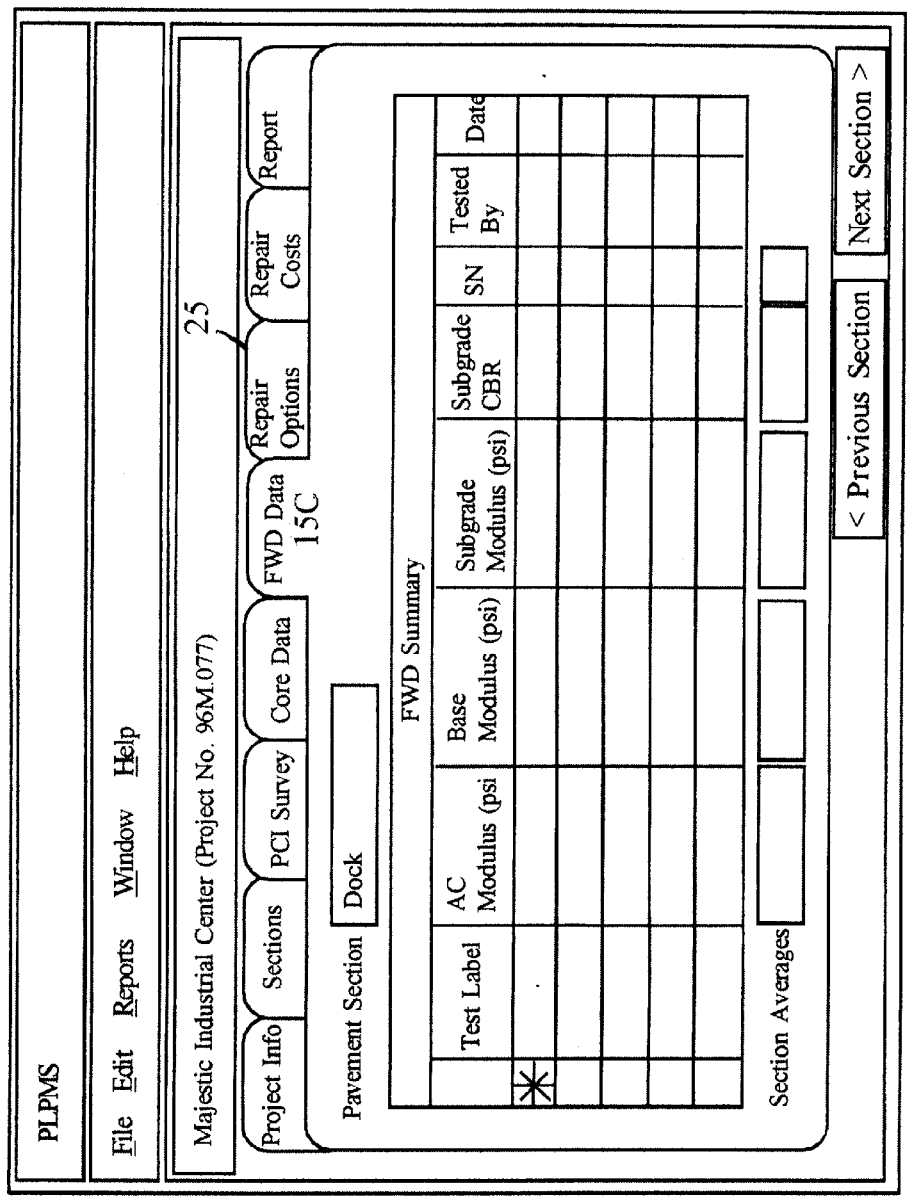
FIG. 9 is the FWD Data entry and analysis form which must be completed for a comprehensive Level 3 analysis.

If the user wishes to complete an exhaustive Level 3 analysis, he must additionally select the third of the three PCI Survey tabs 15C. This opens the FWD Data entry and analysis form of FIG. 9 which must be completed for a comprehensive Level 3 analysis. Again, a <Previous Section button and adjacent >Next Section buttons at lower right allow the user to move between sections, and the current section is identified in a Pavement Section block at top left. To complete the FWD Data Survey form for each section, the user must have completed non-destructive evaluation testing. All FWD data is entered into the FWD Summary section in the center, and this further includes a spread sheet array of fields beginning with a user-selectable Test Label. Following entry of the Test Label, the user indicates the particular AC Modulus (in pounds per square inch), Base Modulus (in pounds per square inch), Subgrade Modulus (in pounds per square inch), the Subgrade California Bearing Ratio (CBR), and structural number (SN). This data is followed by fields indicating Tested By (the surveyor) and the date on which the test was undertaken. The section averages for the AC Modulus, Base Modulus, Subgrade Modulus, the Subgrade California Bearing Ratio (CBR), and SN are shown immediately beneath.

Once all of the Pavement Condition Index Survey/Assessment information has been entered in accordance with the desired Level 1–3 analysis, the user may then proceed to initiate the Repair Options/Decision tree module 200 in order to further analyze data from the Pavement Condition Index Survey/Assessment Module 150. The Repair Options/Decision tree module 200 analyzes the foregoing data and recommends appropriate selections of candidate-maintenance and repair (M&R) options. The Repair Options Index tab 25 initializes to the Repair Options Information Screen of FIG. 10 which reveals an open repair options form. The Repair Options Information Screen of FIG. 10 indicates the recommended maintenance and repair options selected by the Repair Options/Decision tree module 200, and allows manual override to enter alternate repair options.

Figure 10:
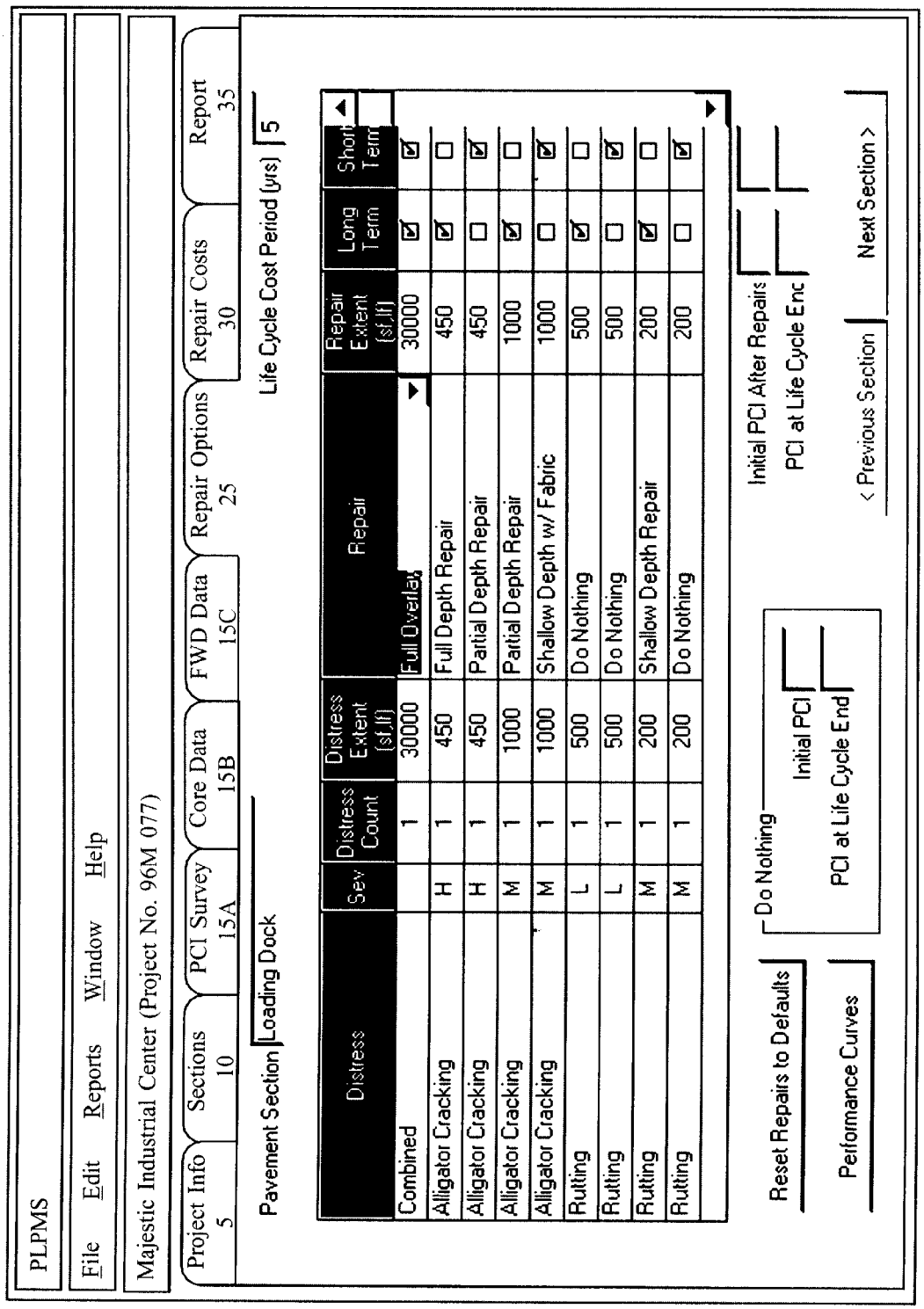
FIG. 10 is the Repair Options Information Screen which indicates the recommended maintenance and repair options selected by the Repair Options/Decision tree module 200.

As shown in FIG. 10, the Repair Options Information Screen provides a section-by section spread sheet recap of information entered in the Pavement Condition Index Survey/Assessment Module 150, and including existing Distress types (Alligator cracking, Bleeding, etc.), Severity (low "L", to medium "M" and high "H"), a Distress Count (indicating number of occurrences), and a Distress Extent (in square feet/linear feet). A "Repair" block follows. Although the Repair block gives a drop-down list of potential repair options, the Repair Options/Decision tree module 200 automatically calculates the recommended repair option for each instance of distress based on all previously input data, and the recommendation is displayed in the Repair block. The selection process that is implemented by the Repair Options/Decision tree module 200 in order to calculate the recommended repair option is an expert system of decision trees that make an appropriate recommendation based on the type of distress, severity, PCI rating, and other factors.

Figure 11:
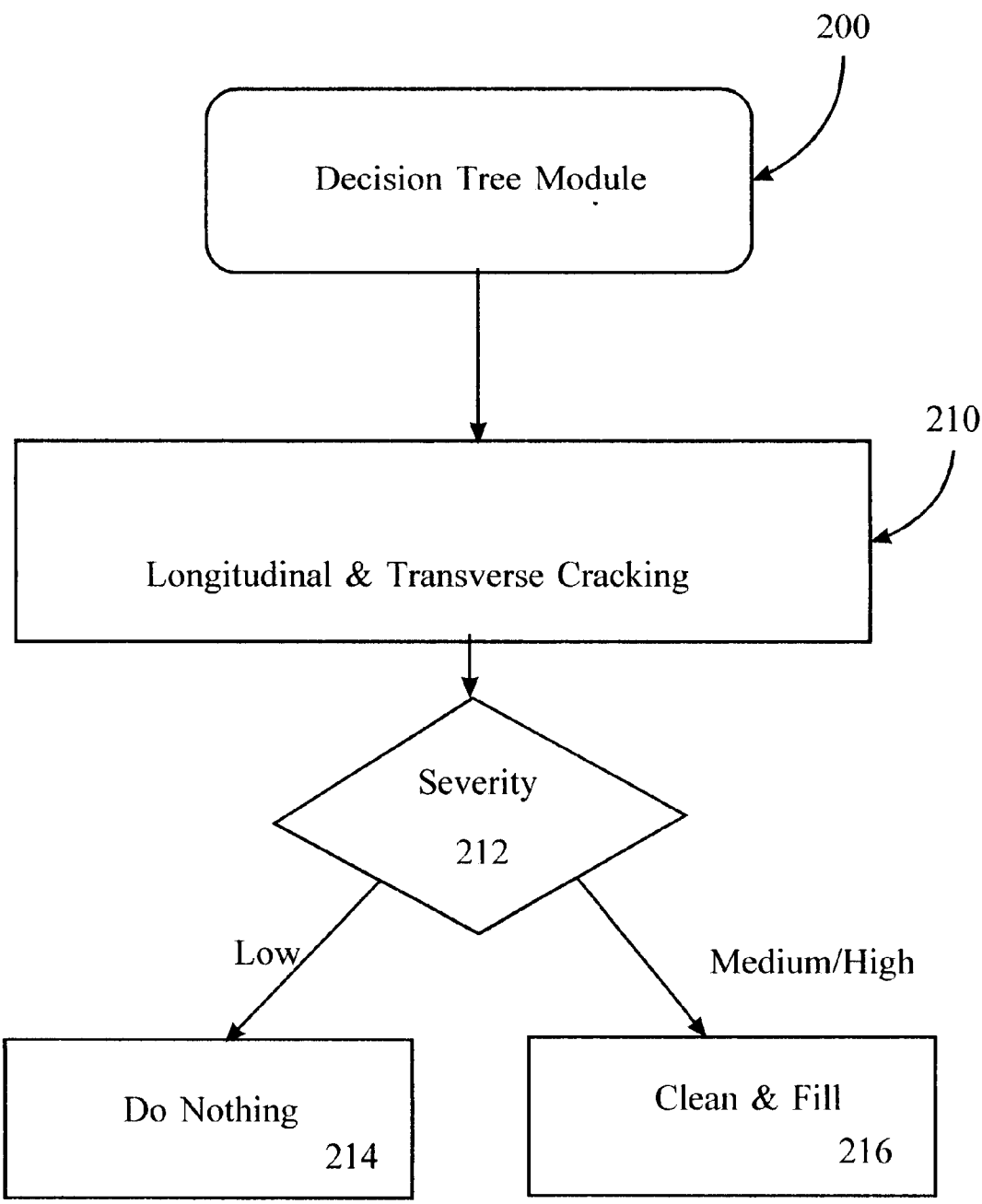
FIG. 11 is the flow-chart decision sequence for longitudinal and transverse (L&T) Cracking.

For example, FIG. 11 illustrates the flow-chart decision sequence for longitudinal and transverse (L&T) Cracking. Where the user has indicated the existence of L&T Cracking in the PCI Survey data entry and analysis form, this is registered by the Repair Options/Decision tree module 200 at step 210. The module then checks the severity of the distress at step 212. If the severity is low, then the module proceeds to step 214 where the recommended repair option displayed in the Repair block of the Repair Options Information Screen of FIG. 10 is "Do Nothing". Alternatively, if the severity is medium or high, then the module proceeds to step 216 where the recommended repair option displayed in the Repair block is "Clean & Fill".

Figure 12:
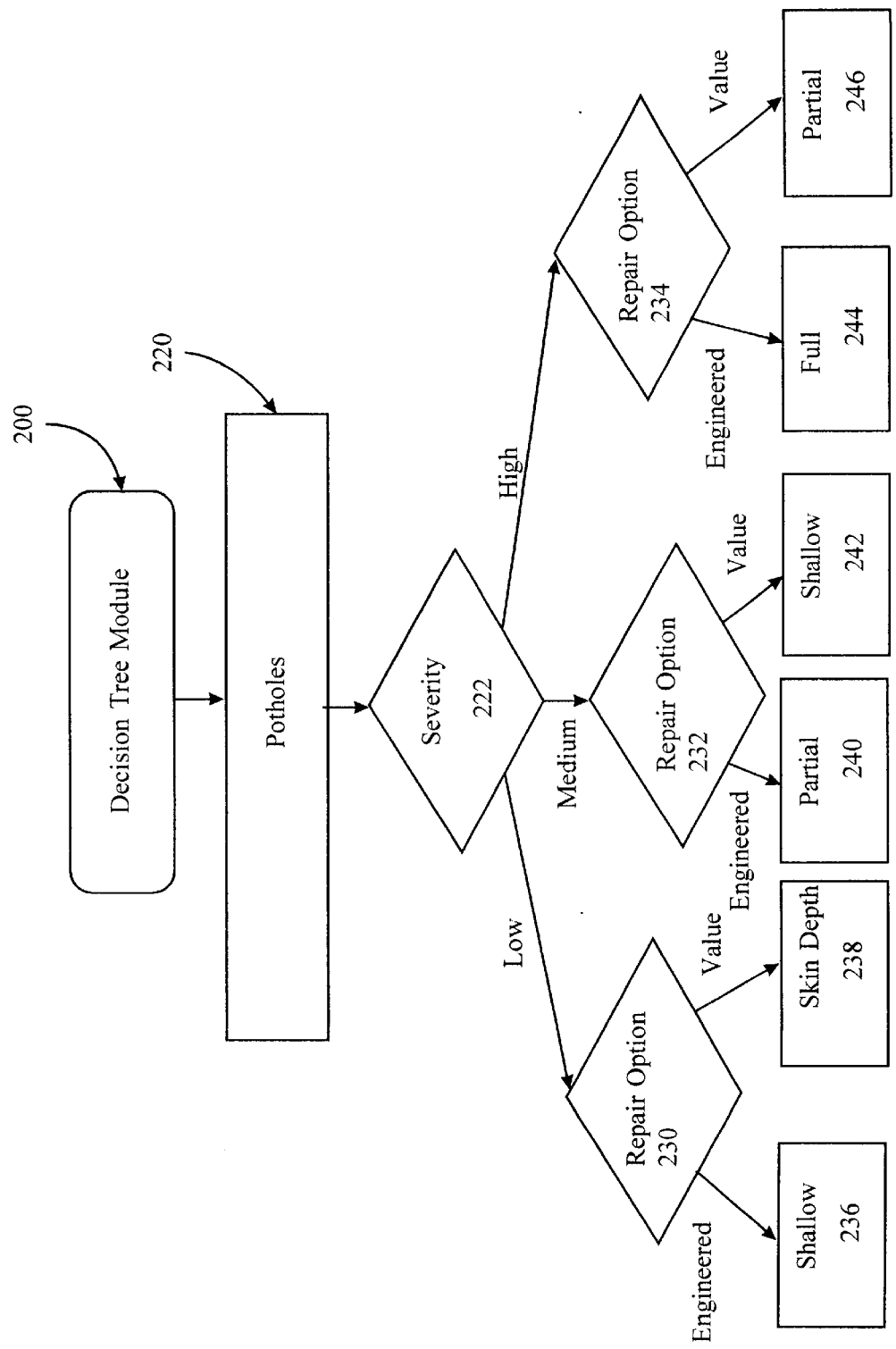
FIG. 12 illustrates the flow-chart decision sequence for Potholes.

FIG. 12 illustrates the flow-chart decision sequence for Potholes. Where the user has indicated the existence of Potholes, this is registered by the Repair Options/Decision tree module 200 at step 220. The module then checks the severity of the distress at step 222. If the severity is low, then the module proceeds to check the Repair Option at step 230 that was selected by the user. If the user selected an Engineered solution, then the module proceeds to step 316 where the recommended repair option displayed in the Repair block is "Shallow". If the user selected a Value solution, then the module proceeds to step 238 where the recommended repair option displayed in the Repair block is "Skin Depth". If the severity is Medium, then the module proceeds to check the Repair Option at step 232 that was selected by the user. If the user selected an Engineered solution, then the module proceeds to step 240 where the recommended repair option displayed in the Repair block is "Partial". If the user selected a Value solution, then the module proceeds to step 242 where the recommended repair option displayed in the Repair block is "Shallow". If the severity is High at step 228, then the module proceeds to check the Repair Option at step 234 that was selected by the user. If the user selected an Engineered solution, then the module proceeds to step 244 where the recommended repair option displayed in the Repair block is "Full". If the user selected a Value solution, then the module proceeds to step 246 where the recommended repair option displayed in the Repair block is "Partial".

Figure 13:
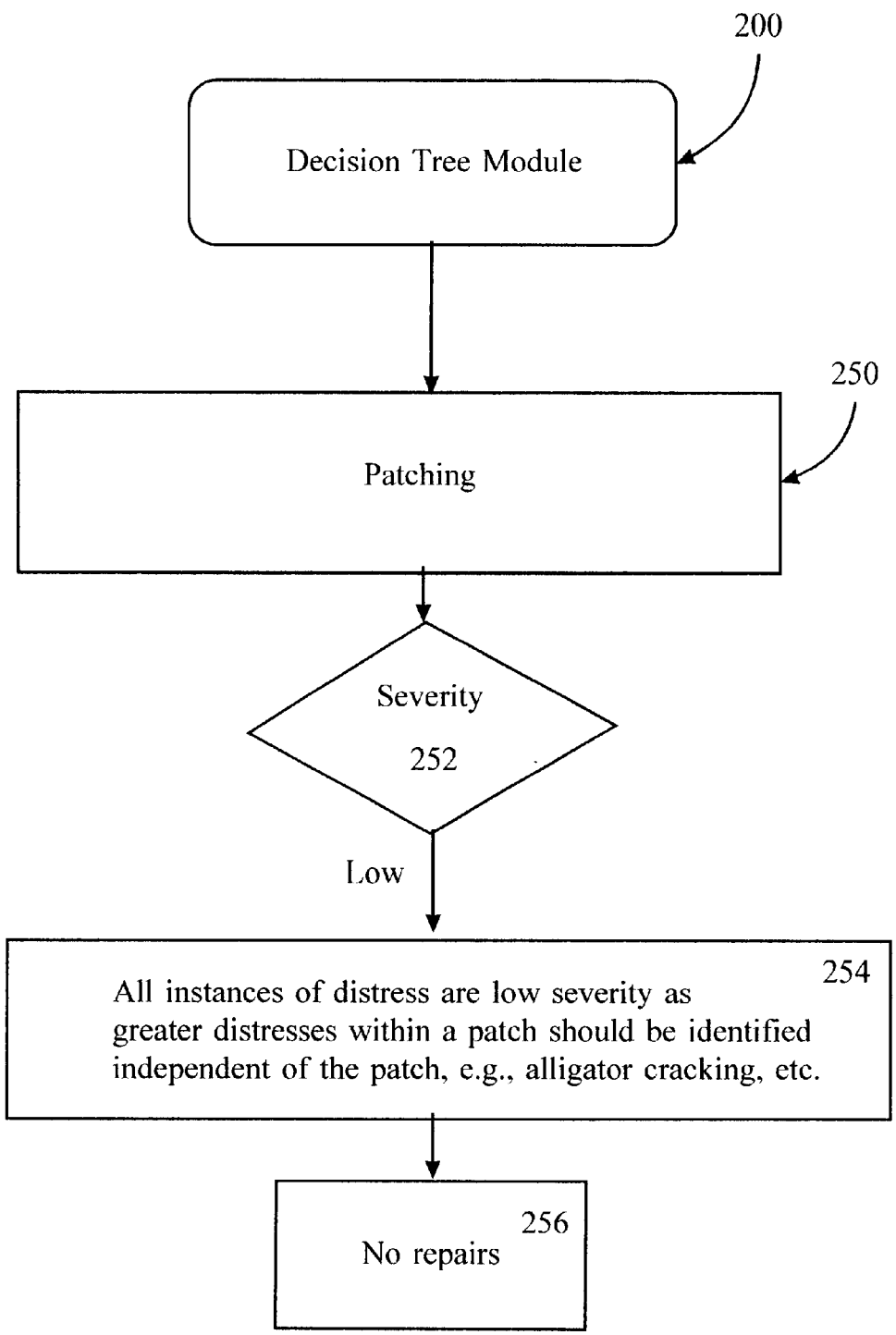
FIG. 13 illustrates the flow-chart decision sequence for Patching.

FIG. 13 illustrates the flow-chart decision sequence for Patching. All instances of patching are considered low severity as anything more should be attributed to a different distress and should be categorized differently (step 254). Thus, the module proceeds to step 256 and the recommendation is no repairs.

Figure 14:
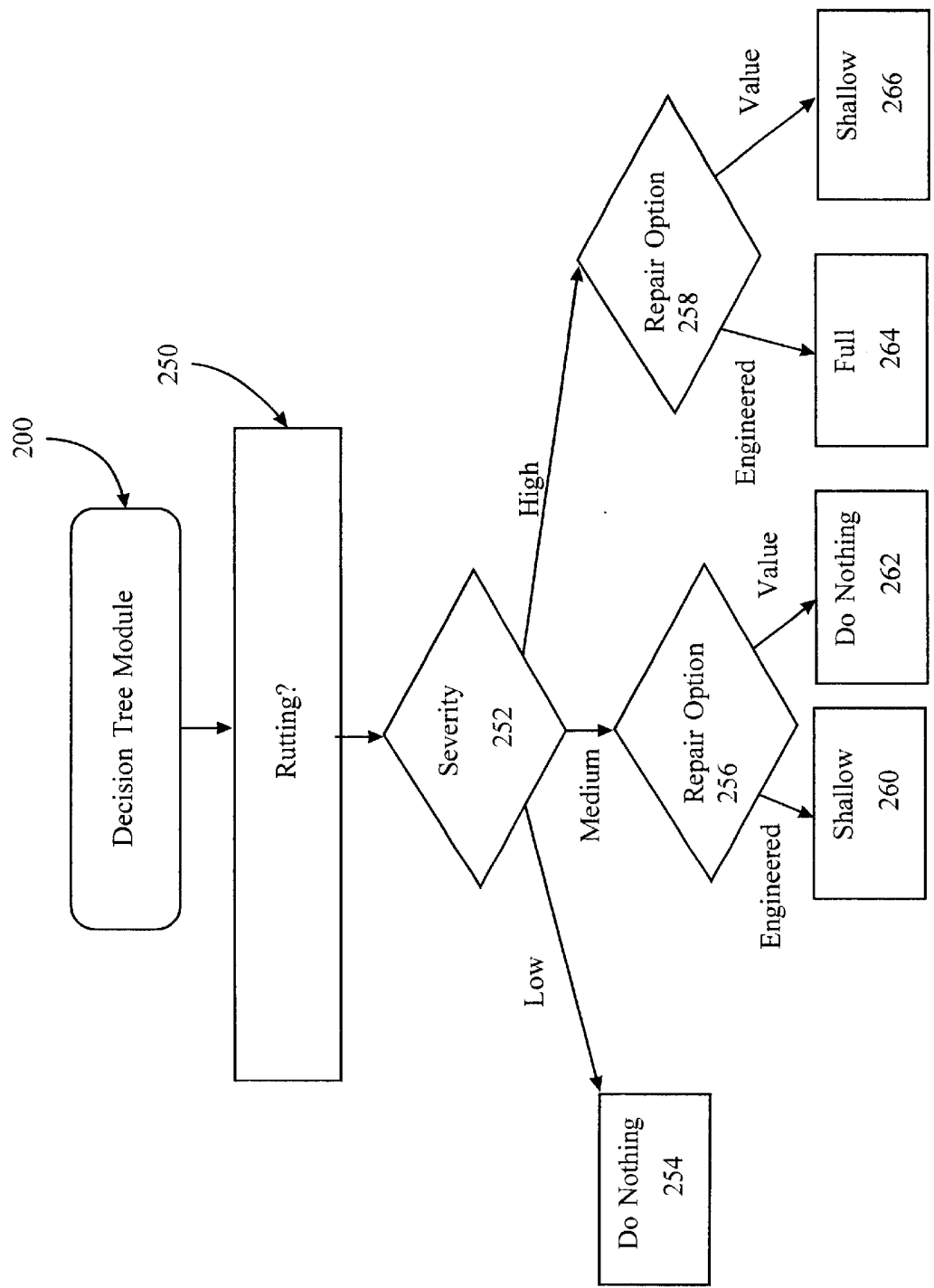
FIG. 14 illustrates the flow-chart decision sequence for Rutting.

FIG. 14 illustrates the flow-chart decision sequence for Rutting. The Repair Options/Decision tree module 200 registers the existence of Rutting at step 250. The module then checks the severity of the distress at step 252. If the severity is low, then the module proceeds to step 254 where the recommended repair option displayed in the Repair block of the Repair Options Information Screen of FIG. 10 is "Do Nothing". Alternatively, if the severity is medium, then the module proceeds to step 256 and checks the Repair Option that was selected by the user. If the user selected an Engineered solution, then the module proceeds to step 260 where the recommended repair option displayed in the Repair block is "Shallow". If the user selected a Value solution, then the module proceeds to step 262 where the recommended repair option displayed in the Repair block is "Do Nothing". Alternatively, if the severity is high, then the module proceeds to step 258 and checks the Repair Option that was selected by the user. If the user selected an Engineered solution, then the module proceeds to step 264 where the recommended repair option displayed in the Repair block is "Full". If the user selected a Value solution, then the module proceeds to step 266 where the recommended repair option displayed in the Repair block is "Shallow".

Figure 15:
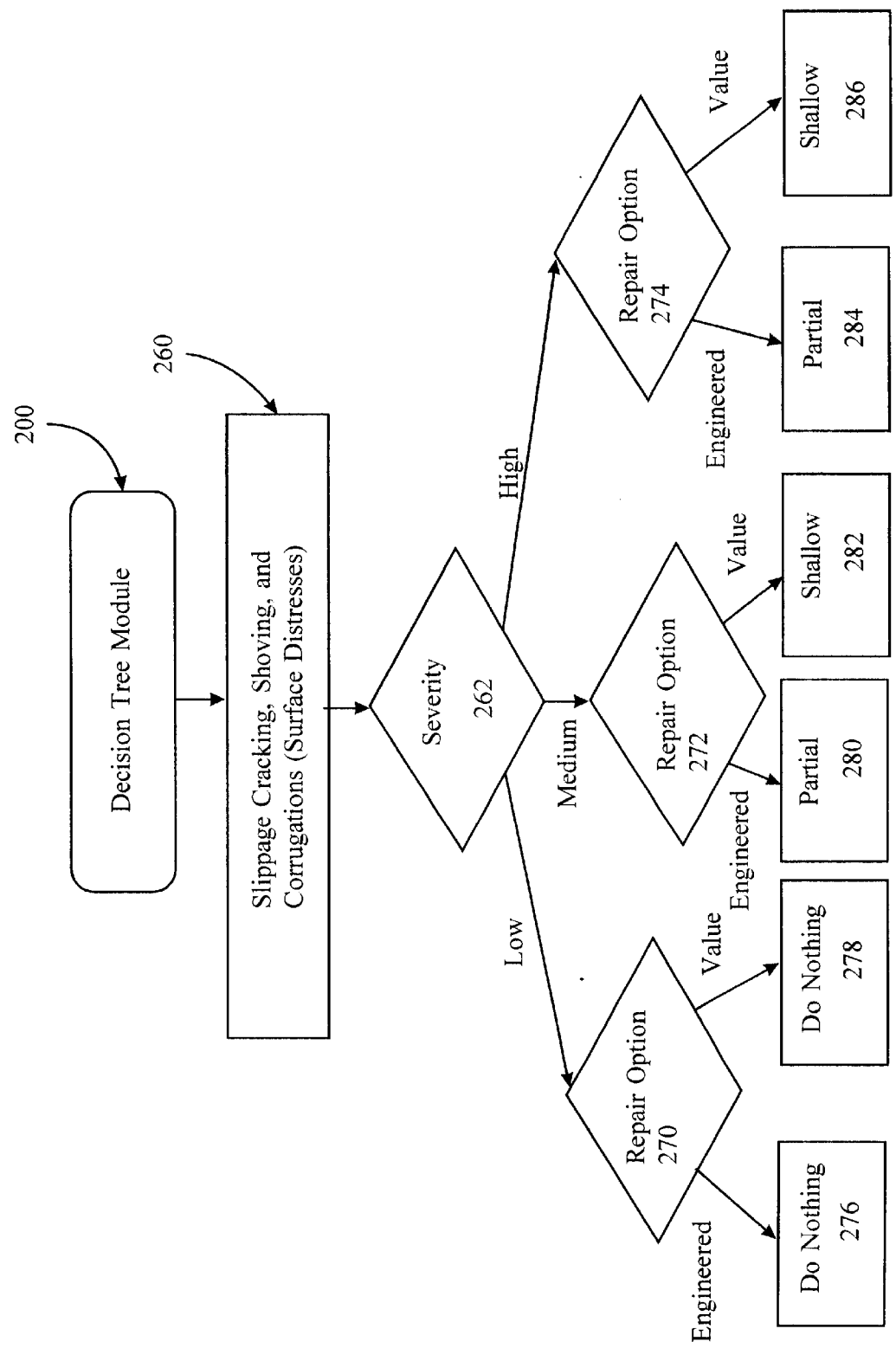
FIG. 15 illustrates the flow- chart decision sequence for Slippage, Cracking, Shoving and Corrugations.

FIG. 15 illustrates the flow-chart decision sequence for Slippage, Cracking, Shoving and Corrugations. The Repair Options/Decision tree module 200 registers the existence of these distresses at step 260. The module then checks the severity of the distress at step 262. If the severity is low, then the module proceeds to check the Repair Option at step 270 that was selected by the user. If the user selected an Engineered solution, then the module proceeds to step 276 where the recommended repair option displayed in the Repair block is "Do Nothing". If the user selected a Value solution, then the module proceeds to step 278 where the recommended repair option displayed in the Repair block is again "Do Nothing". If the severity is Medium, then the module proceeds to check the Repair Option at step 272 that was selected by the user. If the user selected an Engineered solution, then the module proceeds to step 280 where the recommended repair option displayed in the Repair block is "Partial". If the user selected a Value solution, then the module proceeds to step 282 where the recommended repair option displayed in the Repair block is "Shallow". If the severity is High at step 262, then the module proceeds to check the Repair Option at step 274 that was selected by the user. If the user selected an Engineered solution, then the module proceeds to step 284 where the recommended repair option displayed in the Repair block is "Partial". If the user selected a Value solution, then the module proceeds to step 286 where the recommended repair option displayed in the Repair block is "Shallow".

Figure 16:
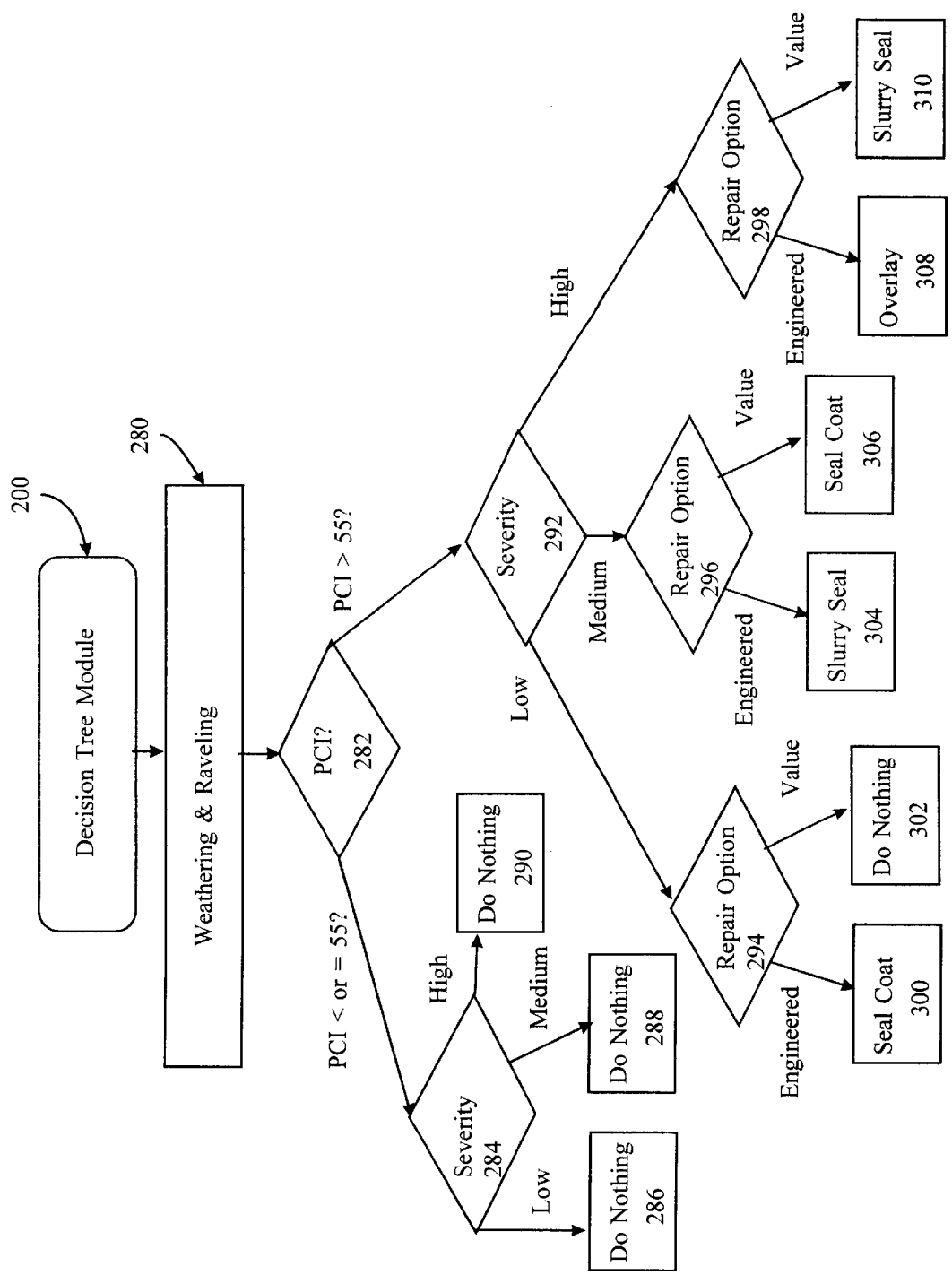
FIG. 16 illustrates the flow-chart decision sequence for Weathering and Raveling.

FIG. 16 illustrates the flow-chart decision sequence for Weathering and Raveling. The Repair Options/Decision tree module 200 registers the existence of these distresses at step 280. The module first checks the PCI index at step 282. If the PCI is less than or equal to 55, program flow proceeds to step 264 where the severity of the distress is considered at step 284. Whether the severity is low, medium or high, the module proceeds to steps 286, 288 or 290 respectively where the recommended repair option is "do nothing". If the PCI is greater than 55, program flow proceeds to step 292 where the module checks the severity of the distress. If the severity is low, then the module proceeds to step 294 where it proceeds to check the Repair Option at step 270 as selected by the user. If the user selected an Engineered solution, then the module proceeds to step 300 where the recommended repair option displayed in the Repair block is "Sealcoaf". If the user selected a Value solution, then the module proceeds to step 302 where the recommended repair option displayed in the Repair block is "Do Nothing". If the severity is Medium, then the module proceeds to check the Repair Option at step 296 that was selected by the user. If the user selected an Engineered solution, then the module proceeds to step 304 where the recommended repair option displayed in the Repair block is "Slurry Seal". If the user selected a Value solution, then the module proceeds to step 306 where the recommended repair option displayed in the Repair block is "Sealcoat". If the severity is High at step 292, then the module proceeds to check the Repair Option at step 298 that was selected by the user. If the user selected an Engineered solution, then the module proceeds to step 308 where the recommended repair option displayed in the Repair block is "Overlay". If the user selected a Value solution, then the module proceeds to step 310 where the recommended repair option displayed in the Repair block is "Slurry Seal".

Figure 17:
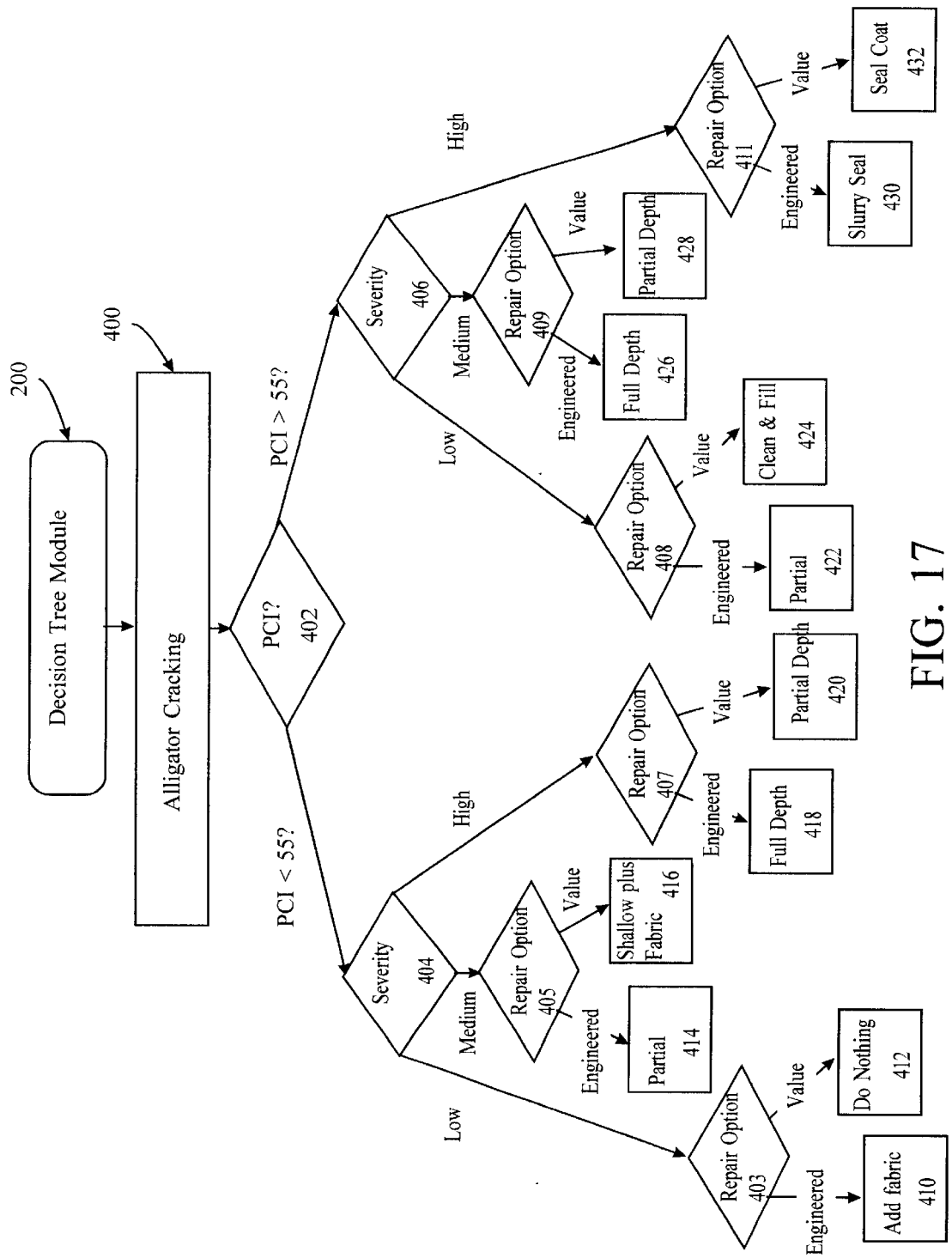
FIG. 17 illustrates the flow-chart decision sequence for Alligator Cracking.

FIG. 17 illustrates the flow-chart decision sequence for Alligator Cracking. The Repair Options/Decision tree module 200 registers the existence of Alligator Cracking at step 400. The module first checks the PCI index at step 402. If the PCI is less than or equal to 55, program flow proceeds to step 404 where the severity of the distress is considered at step 404. If the severity is low, then the module proceeds to check the Repair Option at step 403 as selected by the user. If the user selected an Engineered solution, then the module proceeds to step 410 where the recommended repair option displayed in the Repair block is "Add fabric". If the user selected a Value solution, then the module proceeds to step 412 where the recommended repair option displayed in the Repair block is "Do Nothing". If the severity is Medium, then the module proceeds to check the Repair Option at step 405 that was selected by the user. If the user selected an Engineered solution, then the module proceeds to step 414 where the recommended repair option displayed in the Repair block is "Partial". If the user selected a Value solution, then the module proceeds to step 416 where the recommended repair option displayed in the Repair block is "Shallow plus Fabric". If the severity is High at step 404, then the module proceeds to check the Repair Option at step 407 that was selected by the user. If the user selected an Engineered solution, then the module proceeds to step 418 where the recommended repair option displayed in the Repair block is "Full Depth". If the user selected a Value solution, then the module proceeds to step 420 where the recommended repair option displayed in the Repair block is "Partial Depth".

If the PCI is greater than 55, program flow proceeds to step 406 where the severity of the distress is considered. If the severity is low, then the module proceeds to check the Repair Option at step 408 as selected by the user. If the user selected an Engineered solution, then the module proceeds to step 422 where the recommended repair option displayed in the Repair block is "Partial". If the user selected a Value solution, then the module proceeds to step 424 where the recommended repair option displayed in the Repair block is "Clean and Fill". If the severity is Medium, then the module proceeds to check the Repair Option at step 409 that was selected by the user. If the user selected an Engineered solution, then the module proceeds to step 426 where the recommended repair option displayed in the Repair block is "Full Depth". If the user selected a Value solution, then the module proceeds to step 428 where the recommended repair option displayed in the Repair block is "partial depth". If the severity is High at step 406, then the module proceeds to check the Repair Option at step 411 that was selected by the user. If the user selected an Engineered solution, then the module proceeds to step 430 where the recommended repair option displayed in the Repair block is "Full Depth". If the user selected a Value solution, then the module proceeds to step 432 where the recommended repair option displayed in the Repair block is "Partial Depth".

Referring back to FIG. 10, despite the recommended repair option as calculated above and displayed in the Repair block, the Repair block offers a drop-down list of all repair options and the user is free to override the default selection made by the Repair Options/Decision tree module 200 and make his own recommendation based on engineering experience. The complete list of potential repair options is as follows: Do Nothing, Full Depth, Partial Depth, Shallow Depth, Shallow Depth with Fabric, Skin Depth, Fabric, Slurry Seal, Seal Coat, Clean & Fill Cracks, Full Overlay, Full Reclamation, Full Reconstruction. The user is free to choose any of these in the Repair window.

The Repair Options/Decision tree module 200 also calculates and displays the recommended extent of the repairs in the next adjacent "Repair Extent" block. Again, the user is free to choose to repair more or less pavement than specified.

The Repair Options/Decision tree module 200 also facilitates selection of maintenance and repair (M&R) options. The system allows consideration of three different repair options: Engineered Repair; Value Repair; and Do Nothing.

"Engineered Repair" is based upon repair strategies and pavement design thickness using published industry recommendations.

"Value Repair" represents alternative repair procedures which have been used by the private industry. The long term reliability of some of these repair methods has not been extensively studied, and this option poses a greater degree of risk in the long run.

The third option is to "Do Nothing". This represents the condition of the pavement in the event that no repairs are performed. The present system provides a detailed comparison of the different repair scenarios for all three repair options, and it allows the user to consider the life cycle cost implications for the options. This allows the user to make an informed decision about what type repairs are most appropriate for each particular situation. The Engineered Repair, Value Repair, and Do Nothing options appear as check boxes at the far right two columns. For each instance of distress, the system will automatically place a check in the available repair options. The user is free to alter the designations to check either or both "Engineered Repair" and "Value Repair" blocks, or none to designate "Do Nothing".

The Repair Option form of FIG. 10 is likewise displayed on a section-by section basis. A <Previous Section button and adjacent >Next Section buttons at lower right allow the user to move between sections, and the current section is identified in a Pavement Section block at top left. A "Reset Repairs to Defaults" button at lower left will erase any hand alterations made to the Repair Options, Repair Extent, Short Term or Long Term blocks, and the original auto-selected recommendations from the Repair Options/Decision tree module 200 are restored. A "Performance Curves" button directly beneath provides a gateway to the Chart module 450 for generating bar charts, etc.. The performance curves graphically illustrate the projected pavement performance, by section, for each of the three checked repair options over the life cycle term. The X-axis is time and Y-axis is pavement condition.

A Life Cycle Cost Period window at upper right gives the user-selected life cycle of the pavement section. While the estimated life cycle may be defined by the user, the default number is 5 years. At lower center, a "Do Nothing" section provides a numeric indication of the "Initial PCI" at the beginning of the life cycle, and the "PCI at Life Cycle End". This helps to convey the rate of deterioration of the pavement section if no repairs are undertaken. At lower right, a number of numeric blocks provide an indication of the "Initial PCI After Repairs" assuming that repairs are undertaken, and the "PCI at Life Cycle End". Both the "Initial PCI After Repairs" and the "PCI at Life Cycle End" indicators include two blocks each to show the numbers for both Engineered Repair and Value Repairs for the section. These numbers contrasted to the "Do Nothing" section help to convey the benefit in early repair of the pavement section.

The user may then proceed to examine his expected repair costs. This is accomplished by depressing the "Repair Costs" tab 30 of the Index Tab Interface of FIG. 5. This action initiates the cost module 300 for evaluating the life cycle costs and expected benefits (in terms of extended pavement life) for all candidate M&R activities. The life cycle cost is the sum of the initial cost to do the recommended repairs and the projected "Future cost" to perform additional repairs by the end of the life cycle period (i.e., 5 years). The spreadsheet-like Repair Costs data window as in FIG. 18 comes to the forefront, and a compilation of repair cost is displayed on a section-by-section basis. The Repair Costs data window of FIG. 18 has "Pavement Section" field at the top for identifying the particular section of pavement, e.g., "dock", for which repair cost information is being calculated. A <Previous Section button and adjacent >Next Section buttons at lower right allow the user to move between sections, thereby allowing the user to scroll through the sections of pavement in order to view cost information for each. A number of global variables are shown in the Repair Costs data window of FIG. 18, and these can be changed directly by the user. For instance, the monetary "Discount Rate (%)" can be set at the top to account for the time value of money expenditures (the default is zero). Also, the expected life cycle of the pavement section can be input to the right (default is five years). Underneath these fields, there is a spreadsheet display of estimated repair cost information for the two alternative options; Engineered Repair and Value Repair. This display takes the instance-by-instance repairs entered in the Repair Option form of FIG. 10 and re-categorizes them first by selected option (Engineered Repair/Value Repair), and then by type. Given re-categorization, each necessary type of repair (again as specified in the Repair Options window of FIG. 10) is shown in the appropriate "Repair Field". Further specific repair cost data includes the following:

Repair: identifies each type of repair entered in the Repair Options window as in FIG. 10.

Num: the number of instances that particular type of repair is needed (as indicated in the Repair Options window of FIG. 10).

Area (sf): the cumulative area in square feet for that particular type of repair.

AC Thick: the asphalt thickness.

Base Thick: the pavement base thickness.

Unit Cost: the repair type cost per unit.

Unit: a selectable unit field (square or linear feet).

Base Cost: cost per unit times number of units.

Cost Adjustment: user defined increase or decrease.

Adj. Cost: final cost following user adjustments.

Figure 18:
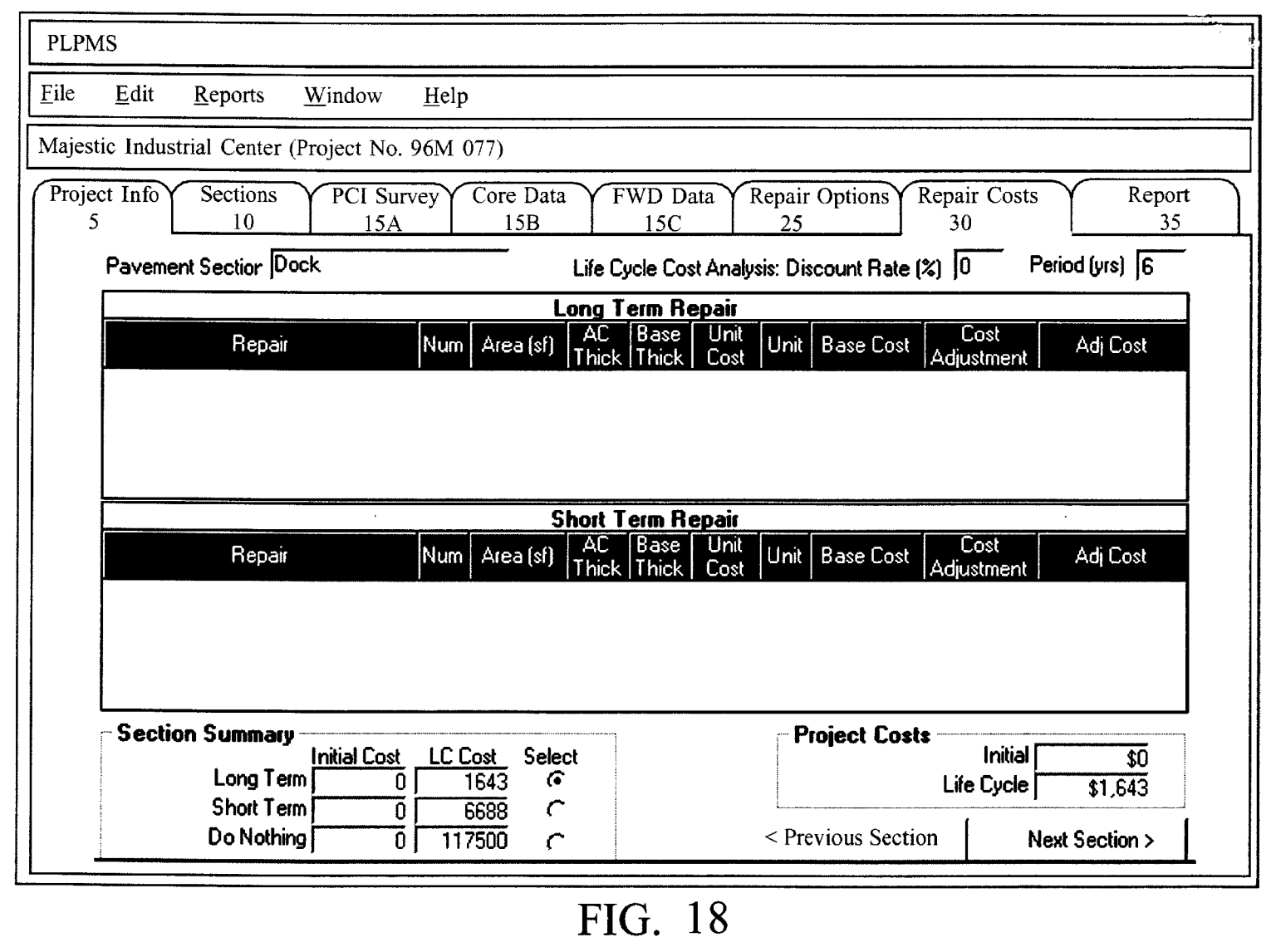

From the above-referenced data, the tabular Section Summary of repair option costs can be calculated and is displayed at lower left in the Repair Costs data window of FIG. 18. The repair cost information includes the "Initial Cost" of repair and the remaining cost over the expected life of the pavement, e.g., the "LC Cost" (Life Cycle Cost). The Select field to the immediate right is configured as a check-box, and this allows the user to select/override the recommended repair option (Engineered Repair, Value Repair, or Do Nothing) for each individual pavement section. Cumulative "Project Cost" information is shown to the lower right, and this is the sum of the section-by-section data shown in the Section Summary table above.

By scrolling through the sections in the Repair Costs Screen of FIG. 18, the user can review, error-check, and modify at will all project information.

Figure 19:
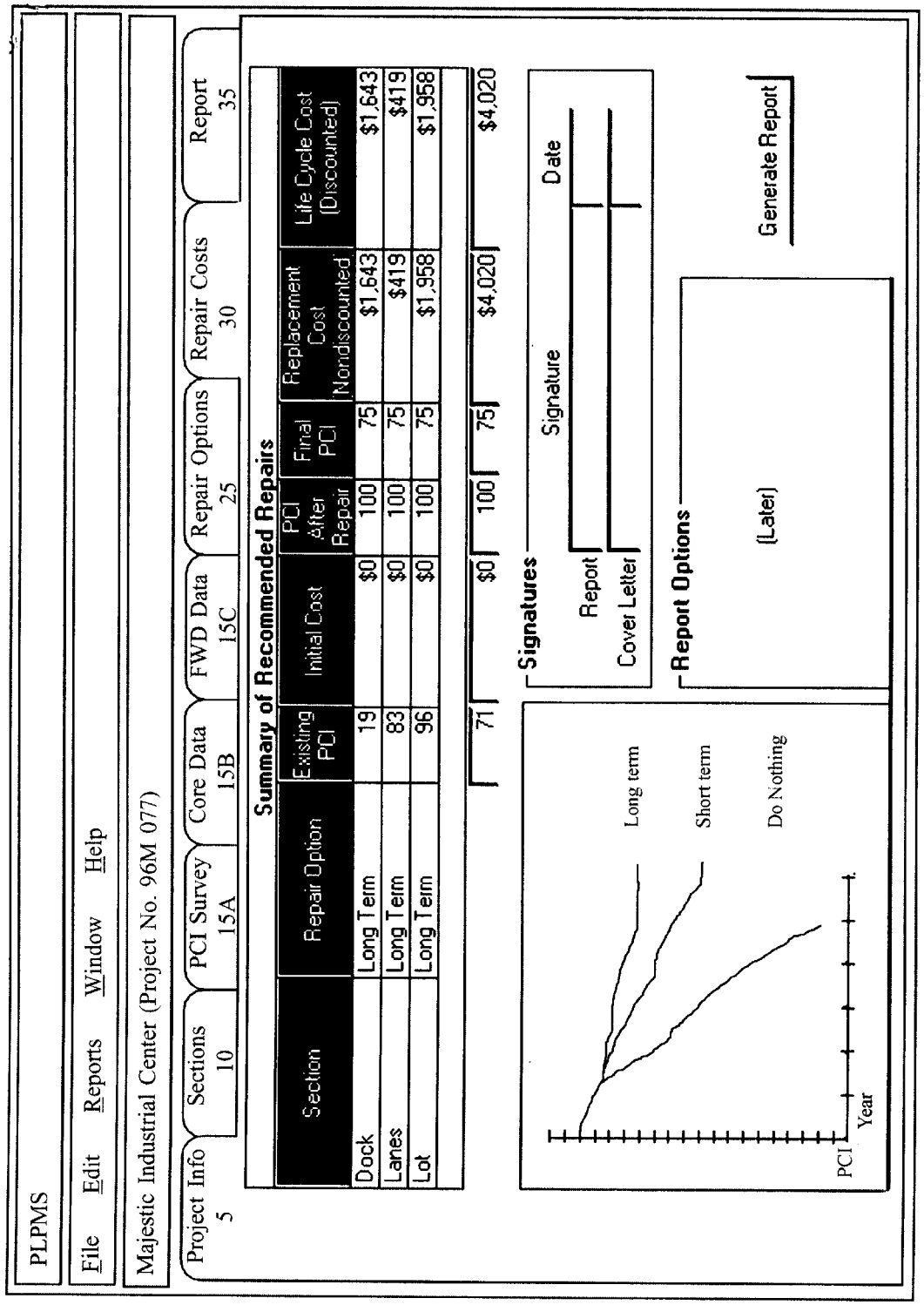
FIG. 19 is the Report Summary window which provides a summary of recommended repairs.

Given the foregoing information, the pavement profile system is capable of generating a report summary for the user. This is accomplished by depressing the "Report" tab 40 of the Index Tab Interface of FIG. 5. This action initiates the report generation module 350, which in turn compiles all preceding information to generate a Report Summary window as shown in FIG. 19. The Report Summary window of FIG. 21 comes to the forefront to show a spreadsheet Summary of Recommended Repairs. The data summarized in the Report Summary window of FIG. 19 includes the following fields:

Section: to delineate the project sections.

Repair Option: to show the user-selected repair option for each section.

Existing PCI: to show the PCI as surveyed.

The "Initial Cost" of repair.

The PCI after the selected repair option has been implemented.

The Final PCI at the end of the designated life cycle.

Replacement Cost: for complete replacement of the section

Life Cycle Cost: initial cost plus future repair cost.

This data is given for each pavement section, and the section columns are totaled to give an overall number beneath the spreadsheet Summary of Recommended Repairs.

In addition, a written report can be generated for the user's customer. For this feature, a "Generate report" button appears at lower right, and respective report and cover letter signature windows allow the user to type in their name for imprinting on the cover letter and report. The "Generate report" button initiates a text generator sub-module 550 that combines the charts, graphs, photographs (e.g., digital photographs) with appropriate narrative for final editing, printout, and presentation to the client. Alternatively, the user can access this same reporting feature from the initial PPS Setup Screen shown in FIG. 3 by selecting Reports > Full Project. An editing sub-module 400 is also available to enable fine-tuning of the system recommendations based upon user experience. The editing module may be any conventional word-processing program such as Microsoft Word, which can be called in a known manner from within the PPS program. The report structure as generated by the text generator sub-module 550 is as follows, and all necessary data is culled from previously described forms:

1.0 TABLE OF CONTENTS 2.0 INTRODUCTION

Explains basic repair cost information as set forth in the description of the background section (above).

3.0 EXECUTIVE SUMMARY

A qualitative description of condition (fair, poor, etc.) with a concise project summary including PCI values, age relative to useful life, maintenance and repair scenarios, and details of costs.

4.0 PROPERTY DESCRIPTION

A description of the project property.

5.0 SCOPE OF WORK

Concise description of the extent of the pavement evaluation performed (Level 1–3).

6.0 PAVEMENT SURVEY

Pavement surveyor.

Pavement surveyor company.

Survey date.

Number of pavement sections

For each pavement section, a section identifier and brief description.

Qualitative summary of condition (fair, poor, etc.) for entire pavement.

For each pavement section:
   Qualitative description of condition.
   PCI rating.
   Overall PCI rating for entire pavement.
   Distresses?
   Description of types of distress.
   % of area covered by distress.
   Indication of medium or high severity
   Observations of previous maintenance
   Methods of treatment 7.0 MATERIALS TESTING (If Level 2 is performed)

Total number of cores and core locations

Numbers of cores and core locations within each pavement

Table of core findings:
   Core location
   Asphalt thickness
   Base thickness/type Subgrade type Total number of soil samples taken For each soil sample:
   Soil type
   General suitability of soil type
   Measured CBR value
   Swell percentage
   Evaluation of CBRI swell
   Maximum compacted soil density
   Optimum moisture content
   Swell value
   CBR scale 8.0 FWD TESTING (If Level 3 is performed)

9.0 DISCUSSION OF RESULTS Life cycle curve for pavement (PCI/Age) with present state indicated.

10.0 DESIGN PARAMETERS

Traffic and soil assumptions 11.0 RECOMMENDATIONS/OPINIONS OF COST

Qualitative general observations/recommendations

Implications of FWD and CBR testing.

Items reported by section:

Items reported by M&R option:

Bullets of recommended M&R activities

Details of M&R activities

Repair section thicknesses and materials
   Overlay thickness
   Graphical comparison of M&R Discussion of relative merits of M&R options
   Design traffic:
      ESALs
      Traffic mix
      Cost estimate for pavement M&R
      Summary of costs w/pavement M&R listed by option
   Items reported for overall pavement:
      Summary of M&R activities and costs for each section and component
      Total cost estimate
      Relevant spec (e.g., VA vs. MD)

10. GLOSSARY OF TERMS

Conventional definitions.

In addition to the report described above, the user can output a limited printed report of only the pavement condition shown above in section 6.0 PAVEMENT SURVEY. This is accomplished from the initial PPS Setup Screen shown in FIG. 3 by selecting Reports >Pavement Condition.

Referring back to the initial PPS Setup Screen shown in FIG. 3 and the five command line options at the top, the user can edit certain pre-defined system set-up parameters and the assumptive data upon which the foregoing analysis and report are based by selecting the Edit command. This begets a drop-down list of further options, including >Repair Unit Costs, >Repair Criteria, & Analysis Parameters.

Upon selecting >Repair Unit Costs, the user is presented with the "Edit Repair Unit Costs" screen shown in FIG. 20. A "Repair Type" block provides a drop-down list at the top that allows the user to select any one of the potential repair options as follows: Do Nothing, Full Depth, Partial Depth, Shallow Depth, Shallow Depth with Fabric, Skin Depth, Fabric, Slurry Seal, Seal Coat, Clean & Fill Cracks, Full Overlay, Full Reclamation, Full Reconstruction. The user is free to choose any of these in the Repair Type block. The pre-defined setup parameters for this type of repair appear in the data blocks below. These include the "Expected Life (yrs)" of the repair, the "Cost Unit" of the repair (e.g., square yards, etc.), and a spread sheet listing of the various "Cost Items" and Associated "Unit Costs" that are included in that repair. Though default values are provided, the user is free to edit the default values as desired. The cost-unit "sy-in" represents square yard-inch (square yards in the plan by inches in depth). The notation "AC" represents asphalt concrete. In this manner, the user can edit all pre-defined repair cost set-up parameters upon which the analysis and report are based for each and every potential repair option.

Upon selecting >Repair Criteria, the user is presented with the "Edit Repair Criteria" screen shown in FIG. 21. Here the user may edit the decision tree criteria used by the Repair Options/Decision tree module 200 in making repair recommendations. The "Edit Repair Criteria" screen of FIG. 21 is a spread sheet listing of all of the possible decision tree criteria for each type of distress. The screen is broken into four distinct sections: "Option 1 (Without Overlay)", "Option 2 (Without Overlay)", "Option 1 (With Overlay)", and "Option 2 (With Overlay)". The With/Without Overlay distinction is necessary because some distresses are repaired in a different manner if an overlay is planned. For each of these four distinct sections, a separate row is provided for each distress type, each distress severity level, each minimum density "Min Dens", each maximum PCI "Max PCI", and each potential repair option. Each separate row spells out the survey parameters under which the Repair Options/Decision tree module 200 will recommend a particular repair option. For instance, viewing the first row of the Option 1 section, when the "Distress" is Alligator Cracking, the Severity "Sev" is High "H", the minimum density "Min Dens" is 0, and the maximum PCI "Max PCI" is 100, the recommended repair option is calculated to be a "Full Depth Repair". With dual reference to FIGS. 21 and 17 (the latter illustrating the flow-chart decision sequence for Alligator Cracking), the Repair Options/Decision tree module 200 employs the decision tree of FIG. 17 whenever the user has entered Alligator Cracking into the Distress Measurements section in the two linked fields "Type" and "Description" of the PCI Survey data entry and analysis form of FIG. 7. The first decision criteria at step 402 is the PCI measurement, the second decision criteria at steps 404, 406 is the severity level, and the third decision criteria at steps 403, 405, 407, 408, 409, 411 is the repair option. The entries in the "Edit Repair Criteria" screen of FIG. 21 determine the above-noted decision criteria. Thus, when the actual survey values indicate that the "Distress" is Alligator Cracking, the Severity "Sev" is Medium "M", the minimum density "Min Dens" is 0, and the maximum PCI "Max PCI" is 100, the Repair Options/Decision tree module 200 will compare the actual entered values against the "Edit Repair Criteria" screen of FIG. 21, and the flow as indicated in the decision tree of FIG. 17 will be PCI>55 at step 402, Severity=Medium at step 406, and the type of repair is Engineered at step 409. Consequently, the recommended repair option is a "Full Depth Repair" as shown in block 426, and in the "Edit Repair Criteria" screen of FIG. 23. All decision tree criteria employed by the Repair Options/Decision tree module 200 are determined in this manner by the entries appearing in the "Edit Repair Criteria" screen of FIG. 21.

Use of the above-described Pavement Profile System affords faster data collection, input and analysis by the user/engineer. Moreover, it allows the user to print a standardized, easy to read, comprehensive report for their customers by which repairs can be timed with pinpoint cost-effectiveness. The report can be easily understood by lay persons.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth herein.

We claim:

1. A method for pavement analysis of commercial and residential parking lots, comprising the steps of:
   collecting actual field survey data to measure existing pavement conditions;
   loading a computer with a software record containing assumptive pavement data regarding present and life cycle conditions;
   inputting said actual field survey data to said software record;
   combining said actual field survey data with said assumptive data to form a pavement profile;
   applying different repair scenarios to said pavement profile to determine life cycle cost implications inclusive of a most cost-effective type of repair for said pavement;
   outputting a most cost-effective type of repair for said pavement so that a user can make an informed decision.

2. The method according to claim 1, wherein said step of inputting said actual field survey data to said software record includes specifying all noted pavement distresses by predefined distress types.

3. The method according to claim 2, wherein said step of inputting said actual field survey data to said software record includes specifying the severity of each specified distress.

4. The method according to claim 3, wherein the severity is specified to be one from among the group of designations comprising low "L", to medium "M" and high "H".

5. The method according to claim 2, wherein said step of inputting said actual field survey data to said software record includes specifying an extent of each distress type in units.

6. The method according to claim 5, wherein said step of combining said actual field survey data with said assumptive data to form a pavement profile further comprises calculating an appropriate deduction from a perfect Pavement Condition Index (PCI) of 100 based on said input actual field survey data.

7. The method according to claim 2, wherein said distress types include Alligator cracking, Bleeding, Block Cracking, Depression, L&T Cracking, Patching, Potholes, Rutting, Slip/Shove/Corrugation, and Weather/Raveling.

8. The method according to claim 1, further comprising the step of generating a standardized comprehensive report containing information to enable a customer to make an informed decision about a cost-effective type of repair.

9. The method according to claim 8, wherein said report discusses existing pavement conditions, life cycle cost analysis, pricing alternatives, and maintenance and rehabilitation design options.

10. The method according to claim 1, wherein said step of applying different repair scenarios to said pavement profile determines and recommends a cost-effective type of repair for each section of said pavement.

11. The method according to claim 10, wherein said step of generating a report allows said user to override the recommended cost-effective type of repair for each section of said pavement.

12. The method according to claim 1, wherein said step of collecting field survey data to measure existing pavement conditions is completed on a section-by-section basis, and said step of applying different repair scenarios is completed on a section-by-section basis to determine life cycle cost implications for an entire job based on different repairs to different sections.

13. The method according to claim 12, wherein said step of collecting field survey data to measure existing pavement conditions is completed on a section-by-section basis, said step of applying different repair scenarios is completed on a section-by-section basis, and said step of combining said actual field survey data with said assumptive data is completed on a section-by-section basis to calculate a Pavement Condition Index for each section as well as an overall project PCI.

14. The method according to claim 1, wherein said step of comparing different repair scenarios further comprises comparing at least three different repair scenarios for life cycle cost implications.

15. The method according to claim 14, wherein said at least three different repair scenarios include an engineered repair scenario based upon published industry recommendations, a less costly value repair scenario, and a do-nothing scenario in which no repairs are performed.

16. The method according to claim 1, wherein said step of inputting said actual field survey data to said software record further comprises filling in a set of forms on said computer which prompt for the appropriate field survey data.

17. A system for pavement analysis of commercial and residential parking lots, comprising:
   a computer including a processor, memory, an operating system, a video display, and an input device;

a software program for loading into memory on said computer, said software program further including,
   a database record containing pre-determined assumptive pavement data,
   a graphical user interface for prompting a user to input actual field survey data regarding existing pavement conditions,
   a compiler for compiling a pavement profile based on said assumptive pavement data and actual field survey data, and for applying different repair scenarios to said pavement profile to determine life cycle cost implications, and
   a report generator for outputting a most cost-effective type of repair for said pavement so that said user can make an informed decision.

18. The system according to claim 17, wherein said graphical user interface includes a series of software forms for prompting a user to input assumptive pavement data regarding present and life cycle conditions, and actual field survey data regarding existing pavement conditions.

19. The system according to claim 18, wherein said software forms prompt said user to input assumptive pavement data and actual field survey data on a section-by-section basis to allow said compiler to compile a pavement profile for each section of pavement and to apply different repair scenarios to each section of pavement, thereby determining sectional life cycle cost implications as well as overall life cycle cost implications for an entire job based on different repairs to various sections.

20. The system according to claim 19, wherein said compiler compares at least three different repair scenarios for life cycle cost implications, inclusive of an engineered repair scenario based upon published industry recommendations, a less costly value repair scenario, and a do-nothing scenario in which no repairs are performed.

21. The system according to claim 20, wherein said assumptive pavement data includes all noted pavement distresses by pre-defined distress types inclusive of Alligator cracking, Bleeding, Block Cracking, Depression, L&T Cracking, Patching, Potholes, Rutting, Slip/Shove/Corrugation, and Weathering/Raveling.

* * * * *